United States Patent
Sinha et al.

(10) Patent No.: US 8,748,457 B2
(45) Date of Patent: Jun. 10, 2014

(54) **2-AMINO-2- [8-(DIMETHYL CARBAMOYL)-8-AZA- BICYCLO [3.2.1] OCT-3-YL]-*EXO*-ETHANOYL DERIVATIVES AS POTENT DPP-IV INHIBITORS**

(75) Inventors: Neelima Sinha, Pune (IN); Prathap Nair, Pune (IN); Navnath Karche, Pune (IN); Nabendu Saha, Pune (IN); Rajan Goel, Pune (IN); Rajender Kumar Kamboj, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/378,941

(22) PCT Filed: Sep. 1, 2009

(86) PCT No.: PCT/IN2009/000478
§ 371 (c)(1),
(2), (4) Date: Dec. 16, 2011

(87) PCT Pub. No.: WO2010/146597
PCT Pub. Date: Dec. 23, 2010

(65) Prior Publication Data
US 2012/0082635 A1   Apr. 5, 2012

(30) Foreign Application Priority Data
Jun. 18, 2009  (IN) .............................. 880/KOL/2009

(51) Int. Cl.
*C07D 451/02* (2006.01)
*A61K 31/46* (2006.01)

(52) U.S. Cl.
CPC .............. *A61K 31/46* (2013.01); *C07D 451/02* (2013.01)
USPC ............................ 514/304; 546/125; 546/126

(58) Field of Classification Search
None
See application file for complete search history.

(56) References Cited

U.S. PATENT DOCUMENTS

| | | | |
|---|---|---|---|
| 5,362,744 A | 11/1994 | Purchase, Jr. et al. | |
| 5,939,560 A | 8/1999 | Jenkins et al. | |
| 6,011,155 A | 1/2000 | Villhauer | |
| 6,166,063 A | 12/2000 | Villhauer | |
| 6,395,767 B2 | 5/2002 | Robl et al. | |
| 6,432,969 B1 | 8/2002 | Villhauer | |
| 6,617,340 B1 | 9/2003 | Villhauer | |
| 6,710,040 B1 | 3/2004 | Hulin et al. | |
| 6,849,622 B2 | 2/2005 | Yasuda et al. | |
| 6,861,440 B2 | 3/2005 | Boehringer et al. | |
| 6,911,467 B2 | 6/2005 | Evans | |
| 7,026,316 B2 | 4/2006 | Ashton et al. | |
| 7,109,347 B2 | 9/2006 | Von Hoersten et al. | |
| 7,132,443 B2 | 11/2006 | Haffner et al. | |
| 7,138,397 B2 | 11/2006 | Yasuda et al. | |
| 7,183,290 B2 | 2/2007 | Haffner et al. | |
| 7,186,731 B2 | 3/2007 | Shima et al. | |
| 7,268,150 B2 | 9/2007 | Hayakawa et al. | |
| 7,332,487 B2 | 2/2008 | Yasuda et al. | |
| 2004/0110817 A1 | 6/2004 | Hulin | |
| 2004/0180925 A1 | 9/2004 | Matsuno et al. | |
| 2005/0038020 A1 | 2/2005 | Hamann et al. | |
| 2005/0070719 A1 | 3/2005 | Belyakov et al. | |
| 2005/0090539 A1 | 4/2005 | Vu et al. | |
| 2005/0130981 A1 | 6/2005 | Aranyl et al. | |
| 2005/0192324 A1 | 9/2005 | Thomas et al. | |
| 2005/0215784 A1 | 9/2005 | Madar et al. | |
| 2005/0234065 A1 | 10/2005 | Hulin et al. | |
| 2005/0261501 A1 | 11/2005 | De Nanteuil et al. | |
| 2006/0205711 A1 | 9/2006 | Himmelsbach et al. | |
| 2006/0258621 A1 | 11/2006 | Campbell et al. | |
| 2006/0276487 A1 | 12/2006 | Aranyi et al. | |
| 2006/0281727 A1 | 12/2006 | Ashton et al. | |

(Continued)

FOREIGN PATENT DOCUMENTS

| | | |
|---|---|---|
| EP | 1 717 225 A1 | 11/2006 |
| EP | 1 719 757 A1 | 11/2006 |
| EP | 1 560 811 | 8/2007 |
| WO | WO98/19998 | 5/1998 |
| WO | WO2004/041795 | 5/2004 |

(Continued)

OTHER PUBLICATIONS

American Heart Association, "Metabolic Syndrome" <http://www.americanheart.org/presenter.jhtml?identifier=4756>, p. 1, (2009).*

(Continued)

*Primary Examiner* — Alicia L Otton
(74) *Attorney, Agent, or Firm* — Erik G. Swenson; Fulbright & Jaworski L.L.P.

(57) ABSTRACT

The present invention is related to novel 2-Amino-2-[8-(dimethyl carbamoyl)-8-aza-bicyclo[3.2.1]oct-3-yl]-exo-ethanoyl derivatives of the general formula (A), their tautomeric forms, their stereoisomers, their pharmaceutically acceptable salts, pharmaceutical compositions containing them, methods of making of the above compounds, and their use as Dipeptidyl Peptidase-IV (DPP-IV) Inhibitors, which are useful in the treatment or prevention of diseases particularly Type II diabetes, other complications related to diabetes and other pathogenic conditions in which DPP IV enzyme is involved.

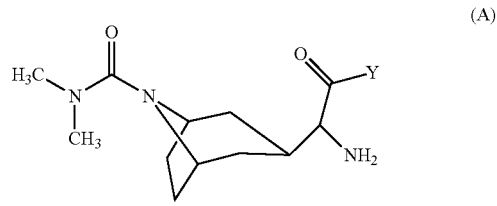

(A)

7 Claims, No Drawings

(56) References Cited

U.S. PATENT DOCUMENTS

| | | |
|---|---|---|
| 2006/0281796 A1 | 12/2006 | Edmondson et al. |
| 2007/0021477 A1 | 1/2007 | Edmondson et al. |
| 2007/0093492 A1 | 4/2007 | Jiaang et al. |
| 2007/0112205 A1 | 5/2007 | Fukushima et al. |
| 2007/0167501 A1 | 7/2007 | Fukuda et al. |
| 2007/0238753 A1 | 10/2007 | Madar et al. |
| 2007/0265320 A1 | 11/2007 | Fukuda et al. |
| 2008/0015146 A1 | 1/2008 | Edwards et al. |

FOREIGN PATENT DOCUMENTS

| | | |
|---|---|---|
| WO | WO2004/052850 | 6/2004 |
| WO | WO 2005/012249 A2 | 2/2005 |
| WO | WO2005/033099 | 4/2005 |
| WO | WO2005/037828 | 4/2005 |
| WO | WO2005/095339 | 10/2005 |
| WO | WO2006/011035 | 2/2006 |
| WO | WO2006/012395 | 2/2006 |
| WO | WO2006/012441 | 2/2006 |
| WO | WO2006/040625 | 4/2006 |
| WO | WO2006/090244 | 8/2006 |
| WO | WO2006/116157 | 11/2006 |
| WO | WO2007/029086 | 3/2007 |
| WO | WO2007/071738 | 6/2007 |
| WO | WO2007/099385 | 9/2007 |
| WO | WO2007/113226 | 10/2007 |
| WO | WO2007/113634 | 10/2007 |
| WO | WO2007/115821 | 10/2007 |
| WO | WO2008/011499 | 1/2008 |
| WO | WO 2009/037719 A1 | 3/2009 |

OTHER PUBLICATIONS

Golub et al. "Molecular Classification of Cancer: Class Discovery and Class Prediction by Gene Expression Monitoring." Science (1999), vol. 286, 521-537.*

Grundy et al. Circulation 112 (2005), pp. 2745-2752.*

Johnson et al. "Relationships between drug activity in NCI preclinical in vitro and in vivo models and early clinical trials." British Journal of Cancer (2001), 84(10), 1424-1431.*

Lala et al. "Role of nitric oxide in tumor progression: Lessons from experimental tumors." Cancer and Metastasis Reviews (1998), 17(1), 91-106.*

Mathur, "Metabolic Syndrome," see section "How is metabolic syndrome defined?" <http://www.medicinenet.com/metabolic_syndrome/article.htm>, pp. 2-3, Mar. 2009.*

Molnar, "New drug policy in childhood obesity," 2005, International Journal of Obesity, 29:S62-S65.*

Sausville et al. "Contributions of Human Tumor Xenografts to Anticancer Drug Development." Cancer Res. 2006, 66(7), Apr. 1, 2006.*

PCT/IN2009/000478 International Search Report and Written Opinion, Feb. 3, 2010, 13 pages.

*Bioorganic & Medicinal Chemistry Letters*, (6(10), 1163-1166 (1996).

D.J. Drucker, *Diab. Care* 30, 1335-1343, 2007.

Deacon, C.F., *Diabetes*, 53, 2181-2189, 2004.

Drucker, D.J., *Cell Metab.* 3, 153-165, 2006.

Drucker, D.J., *J.Clin.Invest.* 117, 24-32, 2007.

Gorrell, M., *Clin. Sci.* 108, 277-292, 2005.

Green, B.D., et al. *Expert Opin. Emerging Drugs*11, 525-539, 2006.

I. Idris and R. Donnelly, *Diab.Obes.Metab.* 9, 153-165, 2007.

Lankas, G.R., et al. *Diabetes* 54, 2988-2994, 2005.

Matthaei, S., et al. *Endocrine Rev.* 21, 585-618, 2000.

McIntosh, C.H.S., et al. *Int. J. Biochem.* Cell Biol. 38, 860-872, 2006.

P.L. Brubaker, *Trends Endocrinol. Metab.* 18, 240-245, 2007.

Frias, J. and S.V. Edelman. *Curr. Opin.Endocrinol. Diab.Obes.* 14, 269-276, 2007.

Sebokova, E., et al. *Curr. Top. Med. Chem.* 7, 547-555, 2007.

Skyler, J.S. *J.Med.Chem.* 47, 4113-4117, 2004.

Wild, S., etal. *Diab. Care* 27, 1047-1053, 2004.

Yach, D., et al. *Nat. Med.* 12, 62-66, 2006.

* cited by examiner

2-AMINO-2-[8-(DIMETHYL CARBAMOYL)-8-AZA-BICYCLO [3.2.1] OCT-3-YL]-*EXO*-ETHANOYL DERIVATIVES AS POTENT DPP-IV INHIBITORS

CROSS-REFERENCE TO RELATED APPLICATIONS

This application is a Section 371 National Stage Application of International No. PCT/IN2009/000478, filed Sep. 1, 2009, and published as WO 2010/146597 on Dec. 23, 2010, which claims priority from the India Application 880/KOL/2009, filed Jun. 18, 2009, the contents of which are incorporated herein in their entirety for all purposes.

FIELD OF THE INVENTION

The present invention is related to novel compounds of the general formula A, their stereoisomers, their racemates, their pharmaceutically acceptable salts, pharmaceutical compositions containing them, methods of making the above compounds, and their use as Dipeptidyl Peptidase IV (DPP IV) Inhibitors, which are useful in the treatment or prevention of diseases in which DPP IV enzyme is known to be involved in the pathogenesis. These diseases include mainly type II diabetes and related diseases such as, syndrome X which includes insulin resistance, hypertension, obesity, dyslipidemia, hyperglycemia, atherosclerosis as well as for the prevention or treatment for other pathogenic conditions in which DPP IV is involved.

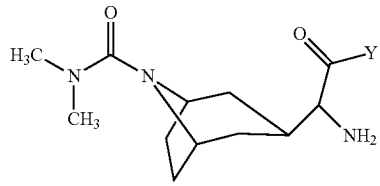

Formula A wherein,

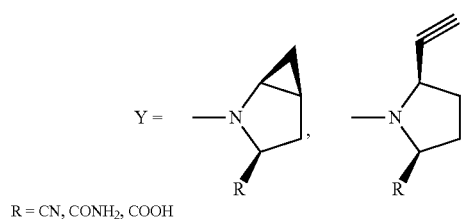

$Y =$ $R = CN, CONH_2, COOH$

BACKGROUND OF THE INVENTION

Diabetes mellitus is a major, growing health problem worldwide (Yach, D., et al. *Nat. Med.* 12, 62-66, 2006). Type 2 diabetes mellitus (hereafter referred as type 2 diabetes, also known as non-insulin-dependent diabetes mellitus, NIDDM) is a heterogeneous disorder, with both genetic and environmental factors contributing to its development. The pathogenesis of type 2 diabetes involves multiple mechanisms leading to hyperglycemia, most notably increased hepatic glucose production, impaired insulin secretion by pancreatic β cells and reduced glucose uptake by skeletal muscle and adipose tissue (peripheral insulin resistance). Type 2 diabetic patients are at substantially increased risks of macrovascular disease including coronary heart disease and stroke and microvascular disease including retinopathy, nephropathy and neuropathy.

Type 2 diabetes is a therapeutic area with huge market potential. The number of diabetic patients is projected to increase from 170-175 million in 2000 to over 350 million by 2030 (Wild, S., et al. *Diab. Care* 27, 1047-1053, 2004; Yach, D., et al. *Nat. Med.* 12, 62-66, 2006). The major part of this numerical increase is expected to occur in developing countries and India will have the distinction of having the largest number of diabetic patients in the world by 2030.

The treatment approaches for type 2 diabetes include diet, exercise, and a variety of pharmacological agents. Clinically established therapies for type 2 diabetes include insulin and its analogs and various oral hypoglycemic agents: sulfonylureas, metformin, α-glucosidase inhibitors (acarbose, miglitol), non-sulfonylurea insulin secretagogues 2(repaglinide, nateglinide) and thiazolidinedione (TZD) derivatives (rosiglitazone, pioglitazone) acting via PPARγ agonism (Matthaei, S., et al. *Endocrine Rev.* 21, 585-618, 2000; Skyler, J. S. *J. Med. Chem.* 47, 4113-4117, 2004). These agents act by different mechanisms to normalize blood glucose levels, but are limited in their abilities, either alone or in combination, to prevent the onset of diabetic complications. Further, each of the above oral agents suffers either from generally inadequate efficacy or number of adverse effects. For example, sulfonylureas, which have been the mainstay of oral treatment for over 5 decades, are known to be associated with a high rate of secondary failure and hypoglycemia. The TZD class of antidiabetic agents (glitazones) improves glucose utilization without stimulating insulin release, but their use is associated with undesirable effects (e.g. risk of myocardial infarction, cardiac hypertrophy, liver toxicity, weight gain).

Considering together the facts that about 90% of all diabetic cases account for NIDDM and the inadequacy of the currently available treatment, the clinical need and market potential for new oral antidiabetic drugs, which maintain tight glycemic control and prevent diabetic diabetic complications are very high.

The recent introduction of incretin-based therapies, which include incretin mimetics (e.g. exenatide) and incretin enhancers (e.g. sitagliptin, vildagliptin) is gaining clinical importance, as novel strategies for the treatment of type 2 diabetes. The incretin concept was first developed based on observations that insulin release was enhanced after oral ingestion of glucose, as compared with an equivalent glucose challenge given intravenously. This led to a hypothesis that in response to nutrient ingestion the gastrointestinal tract released one or more hormones ("incretins") that augmented insulin secretion. This hypothesis was validated with the identification of two key hormones, physiological incretin mimetics, glucagon-like peptide-1 (GLP-1) and glucose-dependent insulinotropic polypeptide (GIP) (Frias, J. and S. V. Edelman. *Curr. Opin. Endocrinol. Diab. Obes.* 14, 269-276, 2007; Drucker, D. J., *J. Clin. Invest.* 117, 24-32, 2007). GLP-1 is released from the enteroendocrine L-cells of the small intestine and GIP is released from duodenal K-cells. These hormones account for about 50% of the total insulin response, following a meal. The discovery of these incretin hormones has stimulated tremendous interest in their therapeutic potential for type 2 diabetes patients.

The incretins, chiefly GLP-1, lower blood glucose levels through multiple mechanisms. GLP-1 potentiates glucose-dependent insulin secretion from islet β-cells by activating specific G-protein-coupled receptors (Drucker, D. J., *Cell*

Metab. 3, 153-165, 2006). In addition to enhancing insulin secretion, GLP-1 also inhibits glucagon secretion and gastric emptying and induces a feeling of satiety leading to weight loss in diabetic patients. More importantly, GLP-1 has the potential to reverse β-cell dysfunction by inhibiting β-cell apoptosis, stimulating β-cell growth and differentiation and promoting β-cell turnover. The incretins also enhance target tissue insulin sensitivity. Incretin-based therapies offer low risk of hypoglycemia, as the activation of incretin receptors is coupled to stimulation of insulin secretion in the presence of elevated blood glucose.

Although GLP-1 is very beneficial in maintaining glycemic control in diabetic patients, the peptide is metabolically unstable, as it is rapidly degraded by the ubiquitous serine protease dipeptidyl peptidase IV (DPP-IV), with an extremely short half-life in vivo, approximately 2 min, thus making it unattractive from the therapeutic standpoint. One approach to circumvent this stability problem has been the development of long-acting degradation-resistant peptides that can be administered parenterally (Deacon, C. F., *Diabetes*, 53, 2181-2189, 2004). This has resulted in the development of exenatide (Byetta, Amylin Pharmaceuticals), a peptidic GLP-1 receptor agonist, that was approved by the FDA for the treatment of type 2 diabetes. Several other long-acting DPP-IV resistant GLP-1 analogs are in clinical development (P. L. Brubaker, *Trends Endocrinol. Metab.* 18, 240-245, 2007). An alternative therapeutic strategy has focused on the inhibition of proteolytic activity of DPP-IV, to prevent the degradation of GLP-1 (and other incretin hormone GIP) and extend its plasma half-life (Green, B. D., et al. *Expert Opin. Emerging Drugs* 11, 525-539, 2006; Sebokova, E., et al. *Curr. Top. Med. Chem.* 7, 547-555, 2007)

Dipeptidyl peptidase IV (DPP-IV, EC 3.4.14.5; also known as CD26), a multifunctional transmembrane glycoprotein, is a serine protease that cleaves N-terminal dipeptides from polypeptides with L-proline or L-alanine at the penultimate position. It is present both in circulation (plasma) and on the surface of several cell types, including epithelial, endothelial and lymphoid cells. It is identical to the T cell activation antigen CD26 and the adenosine deaminase-binding protein. The endogenous substrates of DPP-IV include a wide variety of proline-containing peptides such as growth factors, chemokines, neuropeptides and vasoactive peptides (Gorrell, M., *Clin. Sci.* 108, 277-292, 2005; McIntosh, C. H. S., et al. *Int. J. Biochem. Cell Biol.* 38, 860-872, 2006)

Preclinical studies in laboratory animals, both genetic and pharmacological, have amply demonstrated the essential role for DPP-IV in the control of glucose homeostasis. Mice with a targeted inactivation of DPP-IV gene or Fischer344/CRJ rats with a spontaneous inactivating DPP-IV mutation have increased GLP-1 levels and show improved glucose homeostasis. Furthermore, pharmacological DPP-IV blockade was found to improve glucose tolerance in animal models of impaired glucose tolerance and diabetes (I. Idris and R. Donnelly, *Diab. Obes. Metab.* 9, 153-165, 2007; D. J. Drucker, *Diab. Care* 30, 1335-1343, 2007).

The selectivity of DPP-IV inhibitors against other closely-related proline-specific dipeptidyl peptidases, particularly DPP-8 and DPP-9, has been one of the key issues in the selection of compounds for development, as there is potential for adverse events associated with non-selective DPP-IV inhibitors. The inhibition of DPP-8 and DPP-9 has been found to be associated with toxicities in rat and dog (Lankas, G. R., et al. *Diabetes* 54, 2988-2994, 2005). Therefore, it is important to demonstrate that DPP-IV inhibitors do not appreciably inhibit these closely related enzymes. Consequently, the degree of DPP-8/DPP-9 selectivity has become an important criterion in the selection and development of DPP-IV inhibitors.

Clinically, DPP-IV inhibitors have been found to be very effective in providing glycemic control in diabetic subjects. These molecules are orally bioavailable, prevent degradation of GLP-1 leading to increased circulating levels of hormone and also stabilize other incretins. However, circulating insulin levels are not increased during DPP-IV inhibitor treatment. These inhibitors also improve fasting and postprandial blood glucose levels, as well as effectively lower HbA1c in diabetic patients. They are found to have good tolerability and safety profile during clinical trials and posed low risk of hypoglycemia. Currently, two DPP-IV inhibitors (sitagliptin and vildagliptin) are in clinical use, both as monotherapy and in combination with other antidiabetic agents, such as metformin or thiazolidinediones. Several DPP-IV inhibitors are in advanced stages of clinical development (e.g. alogliptin, saxagliptin, BI-1356, dutogliptin). Several other DPP IV inhibitors are also reported in literature but are different from the compounds of the present invention to be discussed later. Some of such compounds in the prior art are given below:

Earlier development in the filed of DPP IV inhibitors relates to various 2-cyanopyrrolidine derivatives as provided below.

U.S. Pat. No. 5,939,560 and *Bioorganic & Medicinal Chemistry Letters*, 6 (10), 1163-1166 (1996), disclose several compounds of general formula (1) including possessing Dipeptidyl Peptidase IV inhibiting activity and postulated to have therapeutic potential in a number of disease states such as inflammation, graft versus host disease (GVHD), cancer and AIDS. The said research article in *Bioorganic & Medicinal Chemistry Letters* along with the DPP IV inhibitory activity also describes manufacturing methods for 2-cyanopyrrolidides.

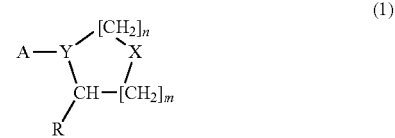

Y = Nitrogen
R = Cyano

Majority of DPP IV inhibitors in the recent inventions pertaining to the class of pyrrolidine derivatives have a common structural feature as provided below:

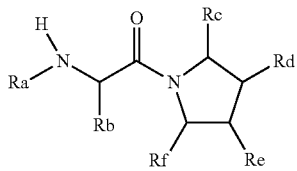

Figure A: Backbone of majority of DPP IV inhibitors

Novartis AG in U.S. Pat. No. 6,011,155; U.S. Pat. No. 6,166,063; U.S. Pat. No. 6,617,340; U.S. Pat. No. 6,432,969 and WO 98/19998 describe the compounds wherein Ra (of figure A) is substituted or unsubstituted alkyl, cycloalkyl, phenoxy, heterocyclic system, heteroaromatic system, [2.2.1] and [3.1.1]bicyclo moiety or adamantly.

(2)

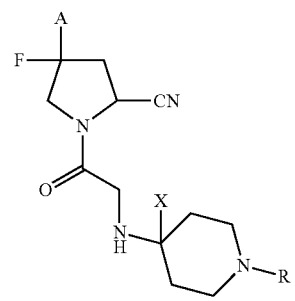

(2A)

- R¹R¹ᵃN(CH₂)ₘ—
  R¹ is substituted or unsubstituted pyridinyl or pyrimidinyl moity; substituted or unsubstituted Phenyl;
  R¹ᵃ is hydrogen or C1-8 alkyl; and m is 2 or 3
- substituted or unsubstituted C3-C12 cycloalkyl;
- substituted or unsubstituted alkyl;
- substituted or unsubstituted phenoxy;
- substituted or unsubstituted heterocyclic, heteroaromatic;
- substituted or unsubstituted [2.2.1] or [3.1.1.] bicyclic moiety;
- substituted or unsubstituted adamantyl U.S. Pat. No. 7,138,397; U.S. Pat. No. 7,332,487 & U.S. Pat. No. 6,849,622 describes various DPP IV inhibitors wherein Ra is a substituted six membered ring as shown below.

(3)

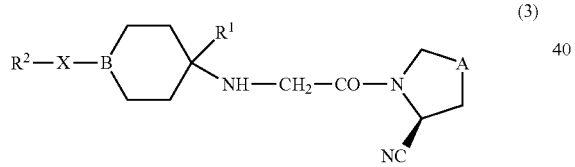

(3A)

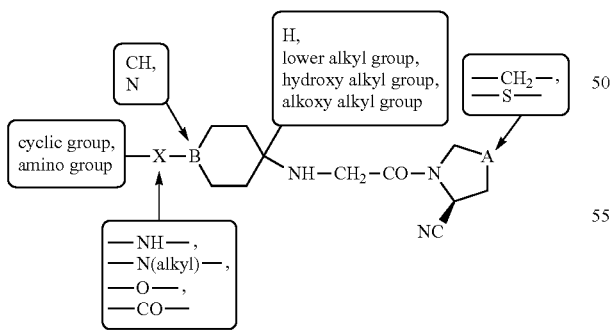

U.S. Pat. No. 7,183,290 describes various fluoropyrrolidines of formulae 4 to 9 as dipeptidyl peptidase inhibitors wherein Re of Figure 'A' is fluoro and of the same figure Ra is selected from various cycles like substituted piperidinyl, pyrrolidinyl, cyclohexanyl, tropanyl, azetidinyl as provided in the compounds 4 to 9.

(4)

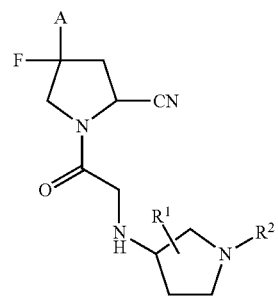

(5)

(6)

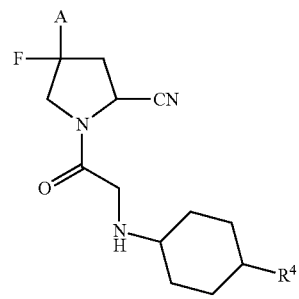

(7)

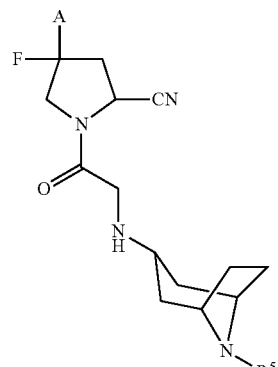

(8)

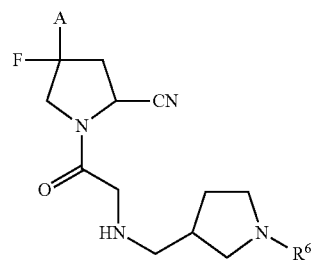

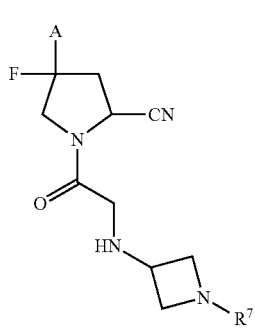

(9)

Following literature on DPP IV inhibitors also provide various substituents at Ra (of Figure A).

U.S. Pat. No. 6,861,440 relates to compounds of formula (10) and pharmaceutically acceptable salts thereof. The compounds are useful for the treatment and/or prophylaxis of diseases that are associated with DPP IV, such as diabetes, particularly non-insulin dependent diabetes mellitus, and impaired glucose tolerance.

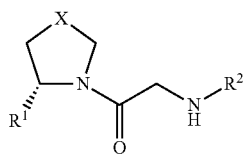

(10)

wherein $R^1$ is CN, $R^2$ is —C($R^3$,$R^4$)—(CH$_2$)$_n$—$R^5$, $R^3$ is hydrogen, lower-alkyl, benzyl, or hydroxybenzyl, $R^4$ is hydrogen or lower-alkyl, $R^5$ is oxazolyl or imidazolyl which can be unsubstituted or substituted with 1 to 3 substituents independently selected from the group consisting of lower-alkyl, lower-alkoxy, halogen, CN, CF$_3$, trifluoroacetyl, pyridinyl and phenyl, which pyridinyl can be unsubstituted or substituted with 1 to 3 substituents independently selected from the group consisting of lower-alkyl, lower-alkoxy, hologen, and CF$_3$, and which phenyl can be unsubstituted or substituted with 1 to 3 substituents independently selected from the group consisting of lower-alkyl, lower-alkoxy, benzyloxy, halogen, CF$_3$, CF$_3$—O, CN and NH—CO-lower-alkyl, X is C($R^8$,$R^9$), $R^8$ and $R^9$ independently from each other are H or lower-alkyl, n is 0, 1 or 2, or a pharmaceutically acceptable salt thereof.

US 20050130981 describes a compound having the formula II as potent DPP-IV enzyme inhibitor.

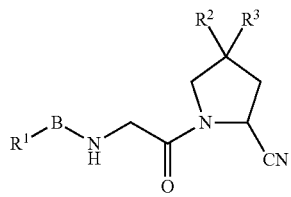

(11)

wherein $R^1$ represents a nitrogen-containing aromatic moiety consisting of one or two aromatic rings; which is optionally mono- or disubstituted by a substituent independently selected from the group consisting of C1-4 alkyl, C1-4 alkoxy, halogen, trihalogenomethyl, methylthio, nitro, cyano, amino, and phenyl group; or $R^1$ represents a thienyl, furyl or benzyl group; or $R^1$ represents a p-toluenesulfonyl group; or $R^1$ represents an acyl group of formula $R_{1a}$—CO, wherein $R_{1a}$ represents a C1-4 alkyl, phenyl, piperidin-1-yl, 4-methylpiperazin-1-yl, pyrrolidin-1-yl; or phenyl, pyridyl or phenylethenyl substituted with one or more groups selected from an alkyl, alkoxy, nitro, or halogen atom; or a phenylethenyl or phenylethyl substituted with alkylene-dioxy; B represents a group having the formula:

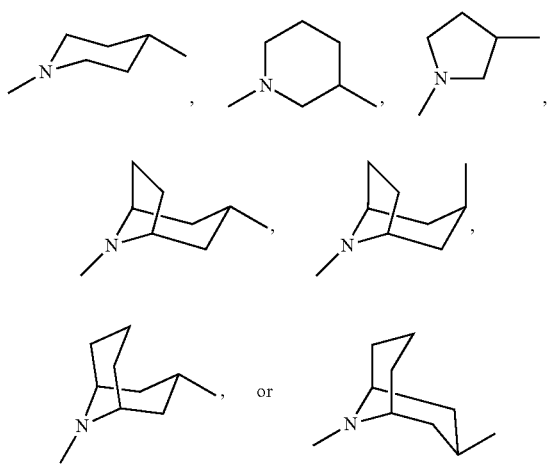

$R^2$ represents a hydrogen atom or a fluorine atom; $R^3$ represents a fluorine atom; or a salt, isomer, tautomer, solvate, or hydrate thereof.

U.S. Pat. No. 7,268,150 discloses a 2-cyano-4-fluoropyrrolidine derivatives of formula 12 having dipeptidyl peptidase IV-inhibiting activity, and a remedy based on the activity for insulin-dependent diabetes (type 1 diabetes), especially for non insulin-dependent diabetes (type 2 diabetes), insulin-resistant disorders, and obesity.

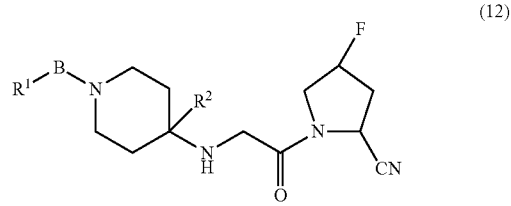

(12)

wherein, $R^1$—B represents methanesulfonyl, formyl or acetyl which may be substituted by a group selected from the group consisting of —OH and fluoro; $R^2$ represents —H, methyl or ethyl; or a pharmaceutically acceptable salt thereof.

US 20050215784 and US 20070238753 disclose compounds of formula (13) that inhibit dipeptidyl peptidase IV (DPP-IV) and are useful for the prevention or treatment of diabetes, especially type II diabetes, as well as hyperglycemia, Syndrome X, hyperinsulinemia, obesity, atherosclerosis, and various immunomodulatory diseases.

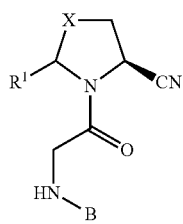

(13)

US20050192324 WO 2006040625, WO 2006011035 and WO 2007099385 describe compound of formula (14) as DPP-IV inhibitors having utility in the treatment of metabolic disorders.

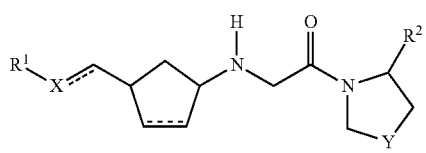

(14)

US20070265320 and US20070167501 describe bicyclo derivatives of formula (15) as DPP-IV inhibitors and claimed to be useful in the prevention and/or treatment of diabetes and associated complications and prevention and/or treatment of other diseases involving DPP-IV.

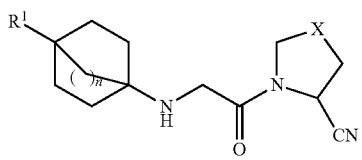

(15)

WO 2005095339 provides compound of formula (16) as DPP IV inhibitors. The compounds were claimed to be useful in the treatment of diabetic complications including diabetic neuropathy, diabetic microangiopathy, and the like.

(16)

US20060276487 relates to the novel compounds of the general formula (17) possessing dipeptidyl peptidase IV enzyme inhibitory activity

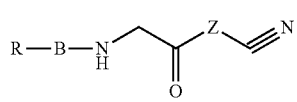

(17)

wherein B is selected from following groups

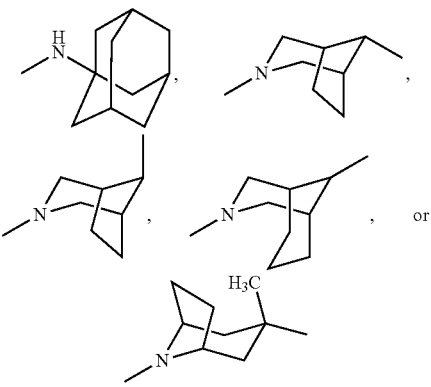

and Z is selected from the groups of formula:

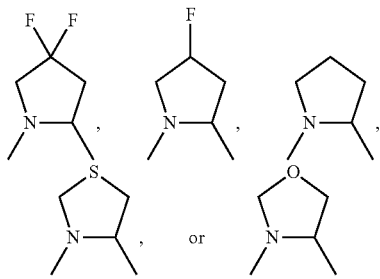

US 20060258621 is directed to pyrrolidinylaminoacetyl pyrrolidine boronic acid compounds of formula (18) that display selective, potent dipeptidyl peptidase IV (DPP-IV) inhibitory activity. These compounds are claimed to be useful for the treatment of disorders that can be regulated or normalized via inhibition of DPP-IV including those characterized by impaired glycemic control such as Diabetes Mellitus and related conditions.

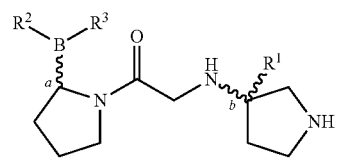

(18)

WO 2006090244 relates to DPP IV inhibitors of formula (19) claimed to be useful in treatment of disorders mediated by DPP IV inhibition, such as diabetes.

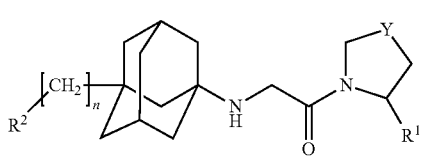

(19)

The second important point of substitution in the backbone provided in figure 'A' is Rb. Substituents at Rb tried by various inventors are summarized hereinbelow.

Invention described in U.S. Pat. No. 7,026,316 is directed to a compound of formula (20), which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

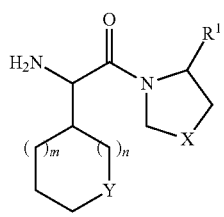

(20)

U.S. Pat. No. 7,132,443 discloses fluoropyrrolidines (compounds of formula 21 and 22, wherein Re of figure 'A' is fluoro) as dipeptidyl peptidase IV inhibitors, their use for inhibiting serine proteases, such as dipeptidyl peptidases, such as DPP-IV and to methods for their production and their therapeutic utility. The inventors specifically claim compound of formula 22.

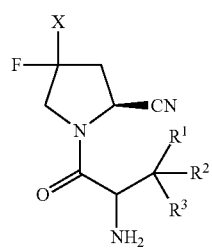

(21)

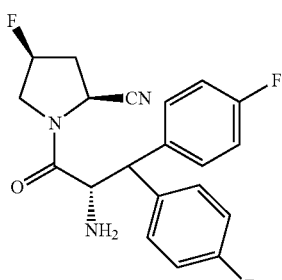

(22)

US 20060281796 provide DPP-IV inhibitors wherein Rb (of Figure A) is fused indole derivative as shown in the formula (23). The compounds were claimed to be useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

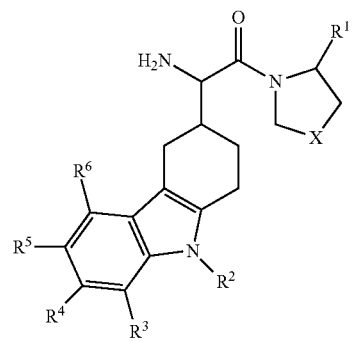

(23)

US 20070021477 is directed to DPP IV inhibitors wherein Rb (of Figure A) is fused cyclohexyl group as provided in the formula (24) and are claimed to be useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

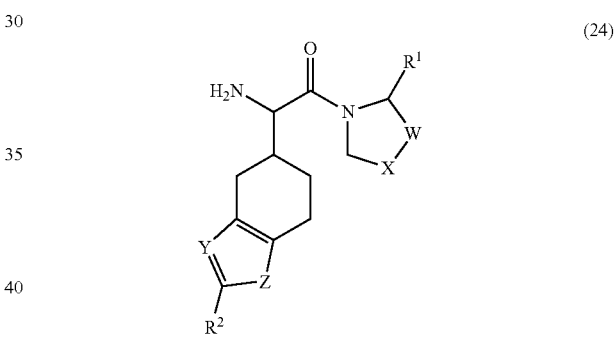

(24)

US 20050234065 provides compounds wherein Rb (of Figure A) is substituted cyclohexyl as shown in the formula (25) as DPP IV inhibitors. The inventors claims the compounds would have utility in the treatment of Type 1 and 2 diabetes, and related diseases.

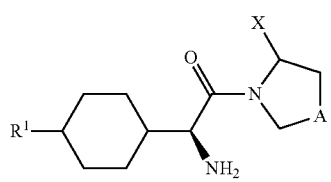

(25)

Some inventors have reported compounds wherein Ra and Rb of the basic backbone provided in figure A both were substituted with various substituents as follows.

U.S. Pat. No. 6,911,467 describes various 1-(2'-aminoacyl)-2-cyanopyrrolidine derivatives of general formula (26) with DP-IV inhibitory activity for treatment of impaired glucose tolerance or type 2 diabetes.

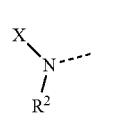

(26)

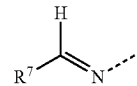

(27)

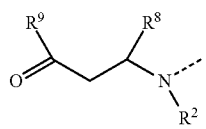

(28)

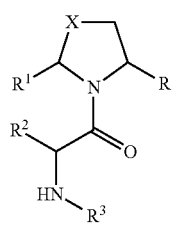

(29)

wherein A is selected from groups (27, 28 and 29); X is selected from aminoacyl groups corresponding to the natural amino acids, acyl groups ($R^3$—CO), $R^4$COOC ($R^5$)($R^6$)OCO, methoxycarbonyl, ethoxycarbonyl and benzyloxycarbonyl; $R^1$ is selected from H, $C_1$-$C_6$ alkyl residues, $(CH_2)_a NHW^1$, $(CH_2)_b COW^2$, $(CH_2)_c OW^3$, $CH(Me)OW^4$, $(CH_2)_d$—$C_6H_4$—$W^5$ and $(CH_2)_e SW^6$, where a is 2-5, b is 1-4, c is 1-2, d is 1-2, e is 1-3, $W^1$ is $COW^6$, $CO_2W^6$ or $SO_2W^6$, $W^2$ is OH, $NH_2$, $OW^6$ or $NHW^6$, $W^3$ is H or $W^6$, $W^4$ is H or $W^6$, $W^5$ is H, OH or OMe, and $W^6$ is $C_1$-$C_6$ alkyl, optionally substituted phenyl, optionally substituted heteroaryl or benzyl and $R_2$ is selected from H and $(CH_2)_n$—$C_5H_3N$—Y, where n is 2-4 and Y is H, F, Cl, $NO_2$ or CN, or $R^1$ and $R^2$ together are —$(CH_2)_p$— where p is 3 or 4; R.sup.3 is selected from H, $C_1$-$C_6$ alkyl and phenyl; $R^4$ is selected from H, $C_1$-$C_6$ alkyl, benzyl and optionally substituted phenyl; $R^5$ and $R^6$ are each independently selected from H and $C_1$-$C_6$ alkyl or together are —$(CH_2)_m$—, where m is 4-6; $R^7$ is selected from pyridyl and optionally substituted phenyl; $R^8$ is selected from H and $C_1$-$C_3$ alkyl; and $R^9$ is selected from H, $C_1$-$C_6$ alkyl, $C_1$-$C_6$ alkoxy and phenyl.

EP 1 560 811 discloses a compound of formula (30) which inhibit dipeptidyl peptidase IV (DPP-IV) and claims to be useful in the prevention or treatment of diabetes, especially type II diabetes, as well as hyperglycemia, Syndrome X, hyperinsulinemia, obesity, atherosclerosis, and various immunomodulatory diseases.

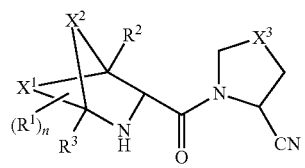

(30)

Literature providing DPP-IV inhibitors wherein, Ra and Rb of the basic backbone provided in figure A become part of a ring is summarized below.

US 20050070719 discloses a compound of Formula 31 and pharmaceutically acceptable derivatives thereof as inhibitors of DPP IV. The compounds were claimed to be useful in the treatment of neurological disorders, diabetes, inflammatory disorders such as arthritis, obesity, osteoporosis, and of such other enumerated conditions as can be treated with inhibitors of DPP IV,

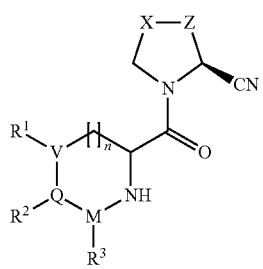

(31)

wherein the pyrrolidine ring formed by X, Z, N, and the carbon atoms to which they are attached, is saturated, or optionally contains one double bond; X is selected from the group consisting of $CH_2$, CH, S, O, NH, N, C=O, $CF_2$, CF, CH—Y, and C—Y; Z is selected from the group consisting of $CH_2$, CH, $CF_2$, CF, C—Y and CH—Y; wherein Y is halogen, hydroxy, or $C_1$-$C_3$ alkyloxy; and wherein one of X or Z must be $CH_2$; or CH if said pyrrolidine ring contains one double bond; M, Q, and V represent carbon atoms; n is 0 or 1; and where either $R^1$ and $R^2$, taken together with V and Q, or $R^2$ and $R^3$, taken together with Q and M, form a 3-6 membered, saturated carbocyclic or heterocyclic ring which may contain one or two heteroatoms selected from the group consisting of O, S, and N.

U.S. Pat. No. 7,186,731 discloses compound of formula (32) having DPP IV inhibiting activity and claimed to be useful in the treatment of conditions mediated by DPP-IV, such as non insulin dependent diabetes mellitus.

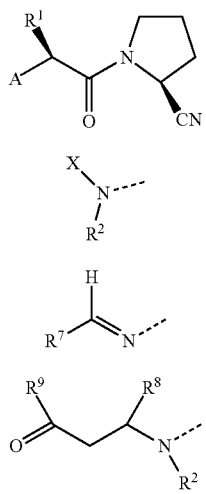

(32)

wherein X1 and X2 each is independently lower alkylene; X3 is +CH2, +CHF or +CF2; R1 is a substituent as described in the patent specification, R2 and R3 each is independently H or lower alkyl; n is 0, 1, 2, 3 or 4.

Pyrrolidine ring expansion, substitution at ring nodes and substitution at rest of the places in the backbone were also tried by various inventors to provide alternative DPP-IV inhibitors.

WO 2004041795 discloses compound of formula (33) as dipeptidyl peptidase IV (DPP-IV) inhibitors, its pharmaceutical compositions and method of treating medical conditions using compound of formula (33). The inventors claim the usefulness of these compounds in the treatment of neurological disorders, diabetes, inflammatory disorders such as arthritis, obesity, osteoporosis, and of such other enumerated conditions as can be treated with inhibitors of DPP-IV.

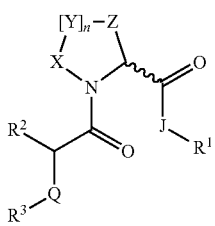

(33)

US 20050090539, US 20050038020 provide adamantylglycine-based inhibitors of dipeptidyl peptidase IV of Formula (34) or a pharmaceutically acceptable salt thereof for the treatment of diabetes and related diseases.

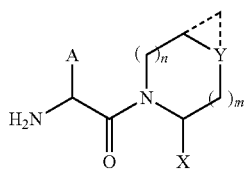

(34)

wherein: n is 0, 1 or 2; m is 0, 1 or 2; the dashed bonds forming a cyclopropyl ring when Y is CH; X is hydrogen or CN; Y is CH, $CH_2$, CHF, $CF_2$, O, S, SO, or $SO_2$ A is substituted or unsubstituted; $R^1$ and $R^2$ are each independently selected from hydrogen, alkyl, alkenyl, alkynyl, aryl and heteroaryl; including pharmaceutically acceptable salts thereof, and prodrug esters thereof, and all stereoisomers thereof.

US 20060281727 describes phenylalanine derivatives of formula (35) which are inhibitors of the DPP-IV enzyme and are claimed to having utility in the treatment or prevention of diseases in with the said enzyme is involved, such as diabetes and particularly type 2 diabetes.

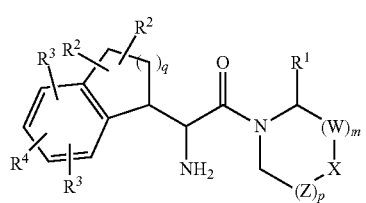

(35)

WO 2007029086 relates to 3-azabicyclo[3,1,0]hexane derivatives of formula (36) as DPP-IV inhibitors.

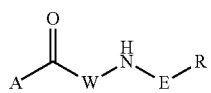

(36)

A is selected from

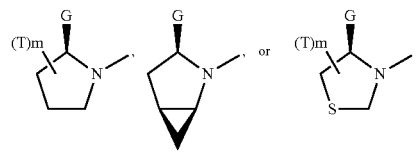

E is substituted or unsubstituted 3-azabicyclo[3.1.0]hexane

In the recent past certain developments pertaining to the class of five membered ring systems like pyrrolidine, thiazolidine, oxothiazolidine and six membered ring systems like piperidine as DDP-IV inhibitors are summarized below.

WO 2006116157, filed by Alantos pharmaceuticals Inc., relates to pyrrolidine and thiazolidine DPP-IV inhibitors claimed to be having utility in the treatment of DPP IV mediated diseases, in particular Type-2 diabetes.

US 20070112205 discloses cyanopyrrolidine derivatives represented formula (37) or a salt thereof

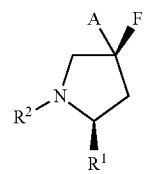

(37)

wherein A is a hydrogen atom or a fluorine atom, $R^1$ is —$CONH_2$ or —CN and $R^2$ is a hydrogen atom, a tert-butoxycarbonyl group, a trityl group, an o-nitrobenzenesulfenyl group, a benzyloxycarbonyl group, a fluorenyloxycarbonyl group, an allyloxycarbonyl group or —C(=O)—$CH_2$—Rc wherein Rc is a halogen atom, a methanesulfonyloxy group, a p-toluenesulfonyloxy group or a hydroxyl group.

US 20040180925 describes various dipeptidylpeptidase-IV inhibitors represented by general formula A-B-D, wherein A represents a substituted or unsubstituted 1-pyrrolidinyl group, a substituted or unsubstituted 3-thiazolidinyl group, a substituted or unsubstituted 1-oxo-3-thiazolidinyl group, or the like; B represents a) a group represented by —(C($R^1$)($R^2$))$_k$CO— (wherein k represents an integer of from 1 to 6, $R^1$ and $R^2$ may be the same or different and each represents a hydrogen atom, a hydroxyl group, a halogen atom, or the like) or the like; D represents —U—V [wherein U represents a substituted or unsubstituted piperazinediyl group or the like, V represents -E-$R^7$ (wherein E represents a single bond, —CO—, —(C=O)O—, or —$SO_2$—; $R^7$ represents a hydrogen atom, a substituted or unsubstituted alkyl group, or the like)] or a pharmacologically acceptable salt thereof.

US 20040110817 discloses inhibitors (compounds of formula 38) of the enzyme dipeptidyl peptidase-IV, pharmaceutical compositions comprising the compounds and the use of such compounds for treating diseases that are associated with proteins that are subject to processing by DPP-IV, such as Type 2 diabetes mellitus, hyperglycemia, impaired glucose tolerance, metabolic syndrome (Syndrome X or insulin resistance syndrome), glucosuria, metabolic acidosis, cataracts, diabetic neuropathy, diabetic nephropathy, diabetic retinopathy, diabetic cardiomyopathy, Type 1 diabetes, obesity, conditions exacerbated by obesity, hypertension, hyperlipidemia, atherosclerosis, osteoporosis, osteopenia, frailty, bone loss, bone fracture, acute coronary syndrome, infertility due to polycystic ovary syndrome, short bowel syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and to prevent disease progression in Type 2 diabetes. The invention also relates to a method of identifying an insulin secretagogue agent for diabetes.

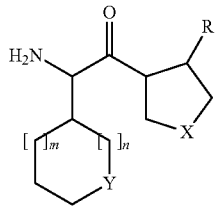

(38)

WO 2005037828 describes pyrrolidine-based compounds of formula (39) having DPP-IV inhibitory activity. The specification also describes the methods of preparing the said compounds and pharmaceutical compositions containing them.

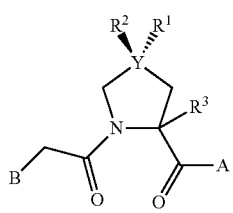

(39)

U.S. Pat. No. 7,109,347 relates to method of treating breast cancer comprising administration of the therapeutically effective amount of an at least one inhibitor of DPP IV, wherein the said inhibitor is an amino acid linked to a thiazolidine or a pyrrolidine group by a peptide bond.

US 20050261501 discloses compounds of formula (40) useful as DPP-IV inhibitors.

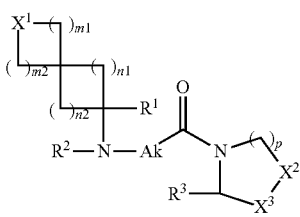

(40)

wherein: $X_1$ represents an atom or group selected from $CR^{4a}R^{4b}$, O, $S(O)_{q1}$ and $NR^5$, wherein $R^{4a}$, $R^{4b}$, $q_1$ and $R^5$ are as defined in the specification, $m_1$ represents zero or an integer from 1 to 4 inclusive, $m_2$ represents an integer from 1 to 4 inclusive, $n_1$ and $n_2$, which may be identical or different, each represent an integer from 1 to 3 inclusive, $R^1$ represents hydrogen or a group selected from carboxy, alkoxycarbonyl, optionally substituted carbamoyl and optionally substituted alkyl, $R^2$ represents hydrogen or alkyl, Ak represents an optionally substituted alkylene chain, p represents zero, 1 or 2, $R^3$ represents hydrogen or cyano, $X^2$ and $X^3$, which may be identical or different, each represent either $S(O)_{q2}$, or $CR^{6a}R^{6b}$, wherein $q_2$, $R^{6a}$ and $R^{6b}$ are as defined in the description, its optical isomers, where they exist, and its addition salts with a pharmaceutically acceptable acid.

US 20070093492 describes pyrrolidine compounds of the formula (41) and methods for using them to inhibit dipeptidyl peptidase IV or treat Type II diabetes. The compounds were claimed to have usefulness in the treatment of type 2 diabetes.

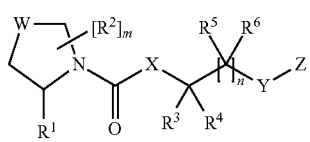

(41)

WO 2007113634 describes compounds represented by formula (42) as DPP IV inhibitors having usefulness in the treatment of type II diabetes and diabetic complications thereof and also in the treatment of dislipidemia, hypercholesterolemia, obesity and hyperglycemia.

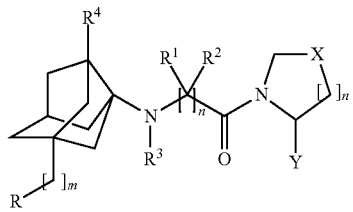

(42)

US 20080015146 describes compound of formula (43) as DPP IV inhibitors and claimed to have utility in the treatment of non-insulin-dependent diabetes mellitus.

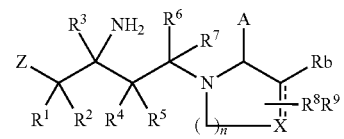

(43)

WO 2005033099 relates to DPP-IV inhibitors of the formula (44), and their analogs, isomers, pharmaceutical compositions and therapeutic uses. Such novel compounds are claimed to be potent and selective inhibitors of DPP-IV, and are effective in treating conditions that may be regulated or normalized via inhibition of DPP-IV. The invention also concerns pharmaceutical compositions comprising the novel compounds of formula (44), methods of inhibiting DPP-IV comprising administering to a subject in need thereof a therapeutically effective amount of said compound and processes for their preparation.

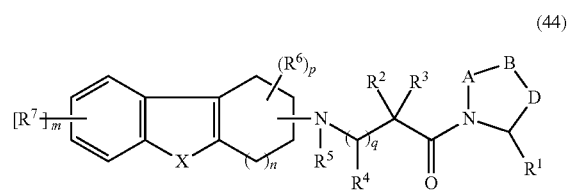

(44)

U.S. Pat. No. 6,395,767 discloses compounds of formula (45) as dipeptidyl peptidase IV (DP 4) inhibitors.

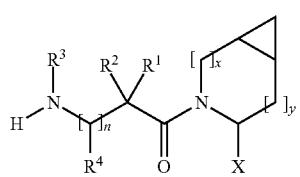

(45)

where x is 0 or 1 and y is 0 or 1 (provided that x=1 when y=0 and x=0 when y=1); n is 0 or 1; X is H or CN. A method is also provided for treating diabetes and related diseases, especially Type II diabetes, and other diseases; employing such DP 4 inhibitor or a combination of such DP 4 inhibitor and one or more of another antidiabetic agent such as metformin, glyburide, troglitazone, pioglitazone, rosiglitazone and/or insulin and/or one or more of a hypolipidemic agent and/or anti-obesity agent and/or other therapeutic agent.

Various Xanthine type molecules were also found to have DPP-IV inhibitory activity as evident from following literature.

US 20060205711 relates to substituted xanthines of general formula (46) wherein $R^1$ to $R^4$ are defined as in the specification, which have an inhibiting effect on the activity of the enzyme dipeptidylpeptidase-IV (DPP-IV).

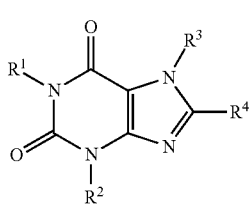

(46)

WO 2007071738 describes deazaxanthine and deazahypoxanthine compounds, of formula (47), wherein X is —CH= and Y is =N—; or X is —C(O)— and Y is —NR³)—; The compounds may be useful in the therapy of diseases and conditions in which dipeptidylpeptidase-IV (DPP-IV) is implicated. The compounds were disclosed to have DPP IV inhibitory activity and claimed to have utility in the treatment of diabetes.

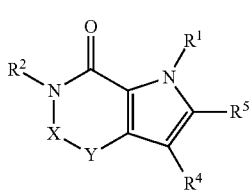

(47)

Compounds from other chemical class shown to have DPP-IV inhibitory activity are provided below.

U.S. Pat. No. 6,710,040 relates to dipeptidyl peptidase-IV inhibitors of formula (48), pharmaceutical compositions comprising the compounds and the use of such compounds for treating diseases that are associated with proteins that are subject to processing by DPP-IV.

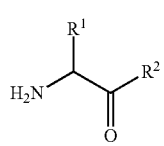

(48)

wherein: $R^1$ is 3-fluoroazetidin-1-yl, 3,3-difluoroazetidin-1-yl, 3,4-difluoropyrrolidin-1-yl, 3,3,4-trifluoropyrrolidin-1-yl, 3,3,4,4-tetrafluoropyrrolidin-1-yl, 3-fluoropiperidin-1-yl, 4-fluoropiperidin-1-yl, 3,4-difluoropiperidin-1-yl, 3,5-difluoropiperidin-1-yl, 3,3-difluoropiperidin-1-yl, 4,4-difluoropiperidin-1-yl, 3,4,5-trifluoropiperidin-1-yl, 3,3,4-trifluoropiperidin-1-yl, 3,3,5-trifluoropiperidin-1-yl, 3,4,4-trifluoropiperidin-1-yl, 3,3,4,5-tetrafluoropiperidin-1-yl, 3,4,4,5-tetrafluoropiperidin-1-yl, 3,3,4,4-tetrafluoropiperidin-1-yl 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl; and $R^2$ is ($C_1$-$C_8$) alkyl or ($C_3$-$C_8$)cycloalkyl.

WO 2006012395 and WO 2006012441 relate to a series of compounds having the general formula (49) as DPP IV inhibitors and claimed to be useful in treatment of diabetes.

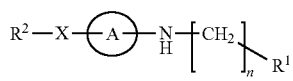

(49)

wherein X is $NR^3$ or O; n is 1 or 2; A is a bicyclic carbocycle and $R^1$ and $R^2$ is as described in the specification.

WO 2007113226 describes compounds of formula (50) for the treatment of non-insulin-dependent diabetes mellitus.

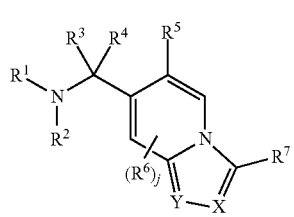

(50)

WO 2007115821 discloses the compounds of formula (51) and their use as DPP IV inhibitors. The compounds were claimed to have utility in the treatment of diabetes and metabolic disorders.

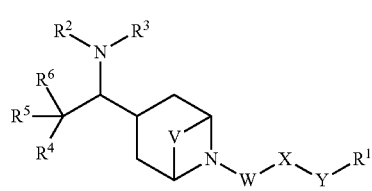

(51)

Though number of compounds were found to posses DPP-IV inhibitory activity, most of the known compounds either lack potency or selectivity.

In search of better candidates having selective DPP-IV inhibitory activity the present inventors designed a series of DPP-IV inhibitors of formula (52) as disclosed in WO2009037719.

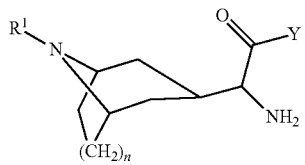

wherein,
n=1, 2
Y is selected from the groups

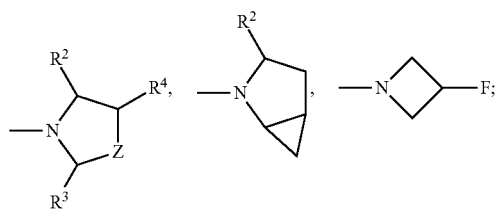

wherein, Z represents $CH_2$, —S—, CHF;
$R^1$ is selected from groups consisting of
i) Hydrogen;
ii) $C_1$-$C_8$alkyl (straight or branched) substituted with 1 to 3 substituents selected from halogens, such as pentyl, trifluoropropyl;

iii) cycloalkyl or cycloalkenyl having 3-10 carbon atoms such as cyclohexyl or cyclohex-2-enyl;
iv) cycloalkylmethyl having 4-10 carbon atoms such as cyclohexyl methyl;
v) Bridged polycycloalkyl methyl having 5 to 12 carbon atoms such as adamantyl methyl;
vi) phenyl which is unsubstituted or substituted with 1-3 substituents each independently selected from cyano or methanesulfonyl;
vii) aralkyl group such as benzyl which is unsubstituted or substituted with 1 to 3 substituents selected from halogens;
viii) heteroaryl group such as pyridyl unsubstituted or substituted with cyano;
ix) heteroaralkyl group such as pyridyl methyl;
x) aralkoxyalkyl group such as benzyloxy ethyl;
xi) $SO_2R^5$; where $R^5$ is methyl, thiophenyl, or phenyl unsubstituted or substituted with 1 to 3 fluoro;
xii) —$CONHR^6$ or —$CSNHR^6$ or —$CONHSO_2R^6$; where $R^6$ is phenyl unsubstituted or substituted with 1 to 3 substituents each independently selected from chloro, fluoro, trifluoromethyl and methoxy;
xiii) $R^7CO$—, wherein $R^7$ is selected from
    a. phenyl unsubstituted or substituted with 1 to 3 substituents selected from halogen, trifluoromethyl, cyano;
    b. benzo[1,3]dioxolyl;
    c. adamantyl;
    d. heteroaryl such as thiophenyl; furyl; pyrazinyl; pyridyl unsubstituted or substituted with a substituent selected from halogen, cyano, methyl, benzyloxy;
    e. N-acetylpiperidinyl;
    f. Cyclohexyl;
    g. Pyridine methyl;
$R^2$ is selected from hydrogen, CN, COOH, or isosteres of COOH, wherein said isosteres of COOH are selected from the groups consisting of esters, tetrazole, acid anhydrides, $CH_2OH$, $CH_2OBn$, CONHOH, $CONH_2$;
$R^3$ is selected from hydrogen, —CN, $C_2$-$C_5$ alkynyl;
$R^4$ is selected from hydrogen or fluoro.

OBJECTIVE OF THE INVENTION

The main objective of the present invention is therefore to provide novel compounds of the general formula A, their tautomeric forms, their stereoisomers, their racemates, their pharmaceutically acceptable salts, pharmaceutical compositions containing them, process and intermediates for the preparation of the compounds given in Formula A which have inhibitory activity against DPP IV Another objective of the present invention to develop novel compounds which are effective and useful to lower increased levels of glucose, lipids, to improve insulin resistance, to decrease body weight, for the treatment and/or prophylaxis of metabolic disorders such as type II diabetes, obesity, hyperlipidemia, with better efficacy and lower toxicity.

SUMMARY OF THE INVENTION

According to one aspect of the present invention there is provided novel organic compounds represented by the general formula (A), their stereoisomers, their racemates, their pharmaceutically acceptable salts, and pharmaceutical compositions containing them or mixture thereof.

In yet another aspect, the present invention provides a process for the preparation of novel organic compounds of the general formula (A), their stereoisomers, their pharmaceutically acceptable salts, and pharmaceutical compositions containing them.

A further aspect of the present invention is to provide novel intermediates, a process for their preparation and their use in methods of making compounds of the general formula (A).

DETAILED DESCRIPTION OF THE INVENTION

In case of all the compounds described in WO2009037719, R1 was never been $(CH_3)_2NC(O)$—. During further work, we interestingly found that when R1 is $(CH_3)_2NC(O)$— the compound has not only improved selectivity during in vitro assay but improved plasma DPP-IV inhibition in Beagle dogs also.

Hence, the novel organic compounds of present invention represented by the general formula (A) is useful for reducing blood glucose, lowering lipid levels, cholesterol and reducing body weight and also have some excellent effects in the treatment and/or prophylaxis of diseases caused by insulin resistance such as type II diabetes, hyperlipidemia, obesity, impaired glucose tolerance, diabetic complications with better efficacy, potency, without or reduced toxicity.

The present invention is related to the compounds of the general formula A in exo configuration,

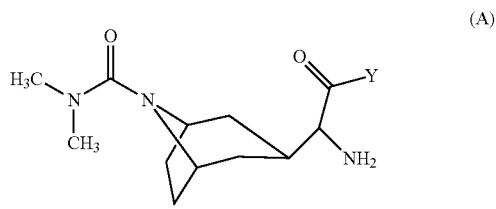

(A)

wherein,

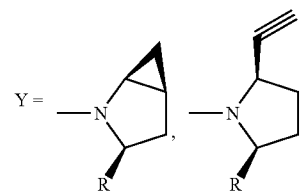

R = CN, $CONH_2$, COOH.

The present invention relates more specifically to compound of formula '1' and '2';

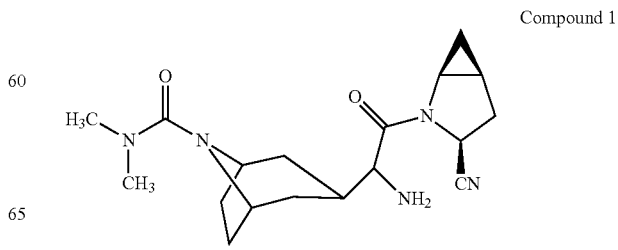

Compound 1

Compound 2

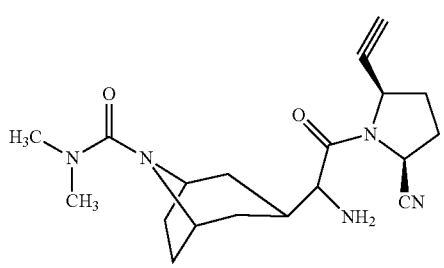

The compounds of the invention were prepared as outlined below according to the methods described herein. However, the invention is not limited to these methods, the compounds may also be prepared as described for structurally related compounds in the literature.

using any standard procedures known to a skilled artisan or by other procedures known in the literature such as in presence of a base such as $K_2CO_3$, $Na_2CO_3$, LiOH in a solvent such as methanol and $H_2O$ at temperature such as 0° C.-30° C. for a suitable time 15-20 hours to obtain the compound of formula III. Compound of formula III was converted to compound of formula V by condensation with compound of formula IV under standard peptide coupling conditions, for example, using EDCI, dicyclohexylcarbodiimide in presence of base such as triethyl amine, diisopropylethylamine and the like. The reaction may also be carried out in the presence of HOBT. The reaction temperature may be in the range between 0-35° C., the duration of reaction may range from 15-30 hours. If R is —$CONH_2$, then —$CONH_2$ group is converted to —CN by treatment of dehydrating agent such as $POCl_3$; if R is —COOH, then such group is converted to —CN by converting it to —$CONH_2$ and then treating the said amide with

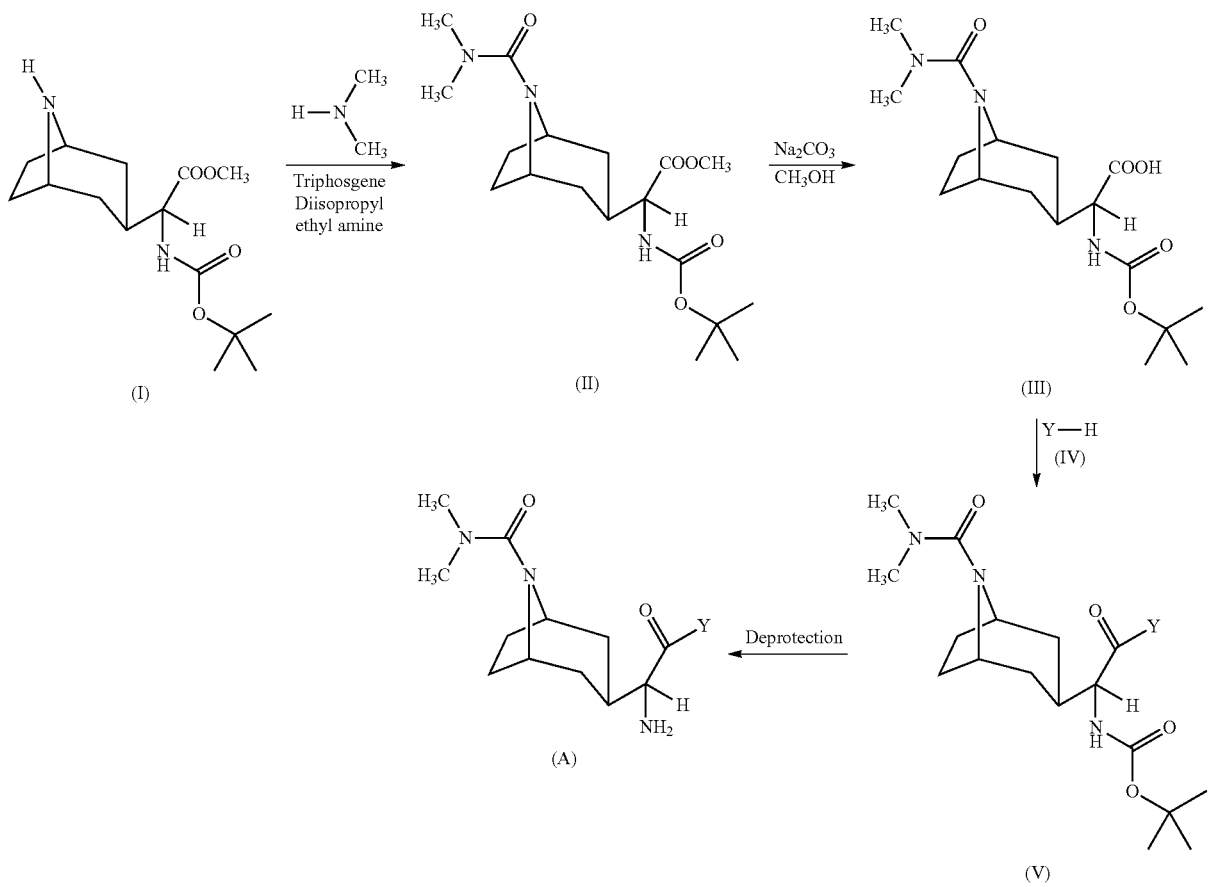

Intermediate I was prepared by the procedure provided in WO 2009/037719 A1. Compound of formula I was converted to compound of formula II by a carbonyl insertion reaction between intermediate I and N,N dimethyl amine using triphosgene and diisopropyl ethyl amine (U.S. Pat. No. 5,362, 744). Other phosgene substitutes such as di-tert-butyl dicarbonate, 1,1-carbonyl his imidazole can also be used. The compound of formula II can also be prepared by treating compound of formula I with dimethyl carbamoyl chloride in halogenated hydrocarbon such as dichloromethane and in presence of base such as triethyl amine or diisopropyl ethyl amine at temperature such as 0° C.-room temperature for a suitable time. The ester group of formula II can be hydrolyzed dehydrating agent such as $POCl_3$. The compound of formula V was further deprotected using common methods known in the art such as using trifluoroacetic acid, in a solvent such as dichloromethane at a temperature 0-30° C. for 30 minutes to one hour to give the compounds of general formula A.

The following examples are provided to further illustrate the present invention and therefore should not be construed to limit the scope of the invention. All $^1$H NMR spectra were determined in the solvents indicated and chemical shifts are reported in δ units downfield from the internal standard tetramethylsilane (TMS) and interproton coupling constants are reported in Hertz (Hz).

EXAMPLE 1

(1S,3S,5S)-2-{(2S)-2-Amino-2-[8-(dimethyl carbamoyl)-8-aza-bicyclo[3.2.1]-oct-3-yl]-exo-ethanoyl}-2-azabicyclo[3.1.0]-hexane-3-carbonitrile trifluoro acetic acid salt (Compound 1)

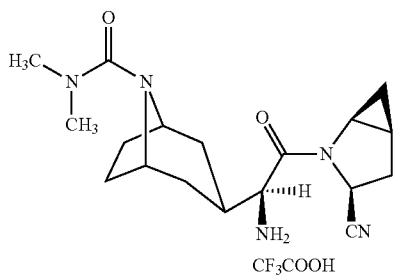 [SMILES: CN(C)C(=O)N1C2CCC1CC([C@H](N)C(=O)N1[C@H](C#N)C[C@@H]3C[C@@H]31)C2 ; "CF3COOH"]

Step 1: Methyl-(2S)-2-(tert-butoxycarbonyl)-amino-2-[8-(dimethyl carbamoyl)-8-aza-bicyclo[3.2.1]-oct-3-yl]-exo-acetate

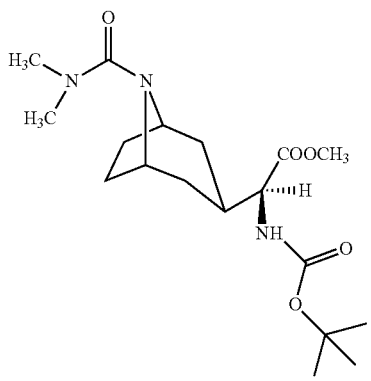 [SMILES: COC(=O)[C@@H](NC(=O)OC(C)(C)C)C1CC2CCC(C1)N2C(=O)N(C)C]

To a stirred and cooled (0° C.) solution of triphosgene (2.0 g, 6.7 mmol) in dichloromethane (100 ml) was added a solution of methyl-(2S)-2-(tert-butoxycarbonyl)-amino-2-[8-aza-bicyclo[3.2.1]-oct-3-yl]-exo-acetate (4.0 g, 13.4 mmol, prepared by following the procedure as described in WO 2009/037719)) and diisopropylethylamine (5.05 ml, 3.78 g., 29.3 mmol) in dichloromethane (50 ml) in a drop-wise manner in 30 minutes. After the addition was completed, the reaction mixture was brought to room temperature and stirred for 30 minutes. This mixture was again cooled to 0° C. and to this was added a solution of 2M solution of dimethyl amine in THF (16.6 ml, 1.51 g., 33.5 mmol) and diisopropyl ethyl amine (5.05 ml, 3.78 g., 29.3 m mol) in dichloromethane (50 ml) in a drop-wise manner (followed a procedure reported in U.S. Pat. No. 5,362,744). The reaction mixture was stirred at room temperature and progress of reaction was monitored by TLC. After completion of reaction, the reaction mixture was concentrated under reduced pressure and diluted with ethyl acetate (250 ml). The organic layer was washed with 5% aqueous solution of $KHSO_4$ (30 ml). The aqueous layer was neutralized to pH 7.0 and extracted with ethyl acetate (3×50 ml). The combined organic layer was dried over anhydrous $Na_2SO_4$. The solvent was concentrated under reduced pressure to get a crude product, which was purified by column chromatography over silica gel (100-200 mesh) using 2% methanol in dichloromethane as an eluent to yield the title compound (3.8 g, 77%).

MS: m/z 370 (M+1)

$^1$H NMR ($CDCl_3+D_2O$, 400 MHz): δ 1.35-1.63 (m, 15H), 1.83-1.92 (m, 2H), 2.12-2.25 (m, 1H), 2.85 (s, 6H), 3.72 (s, 3H), 4.02-4.10 (m, 2H), 4.19 (dd, J=6.0, 8.8 Hz, 1H), 5.04 (d, J=9.2 Hz, 1H),

Step 2: (2S)-2-(tert-Butoxycarbonyl)-amino-2-[8-(dimethyl carbamoyl)-8-aza-bicyclo[3.2.1]-oct-3-yl]-exo-ethanoic acid

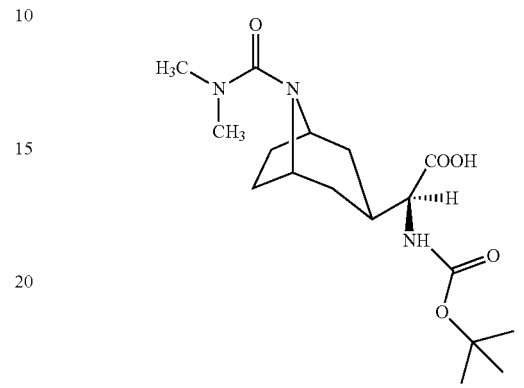

To a stirred and cooled (0° C.) solution of methyl-(2S)-2-(tert-butoxycarbonyl)-amino-2-[8-(dimethyl carbamoyl)-8-aza-bicyclo[3.2.1]-oct-3-yl]-exo-acetate (4.2 g, 11.4 mmol) in methanol (100 ml) was added a solution of $Na_2CO_3$ (6.03 g, 56.9 mmol) in water (100 ml) in a dropwise manner. After the addition was completed, the reaction mixture was stirred at room temperature for 24 hours. The progress of reaction was monitored by TLC. After completion of reaction, the reaction mixture was concentrated under reduced pressure to dryness. To this was added water (50 ml), cooled to 0° C. and pH of the reaction mixture was adjusted to 6.5 with aqueous 10% HCl. The solvent was then removed under reduced pressure to yield a solid, which was stirred with 15% methanol in dichloromethane (3×200 ml) at room temperature for 30 minutes. The reaction mixture was filtered through a buchner funnel and the filtrate was dried over anhydrous $Na_2SO_4$. The solvent was evaporated to yield the title compound (3.5 g., 87%), which was subjected to next step without purification.

MS: m/z 354 (M−1)

$^1$H NMR ($D_2O$, 200 MHz): δ 1.3-1.95 (m, 17H), 2.12-2.40 (m, 1H), 2.86 (s, 6H), 3.65-3.85 (m, 1H), 4.02-4.25 (m, 2H),

Step 3: (1S,3S,5S)-2-{(2S)-2-(tert-butoxycarbonyl)-amino-2-[8-(dimethyl carbamoyl)-8-aza-bicyclo[3.2.1]-oct-3-yl]-exo-ethanoyl}-2-azabicyclo[3.1.0]-hexane-3-carboxamide

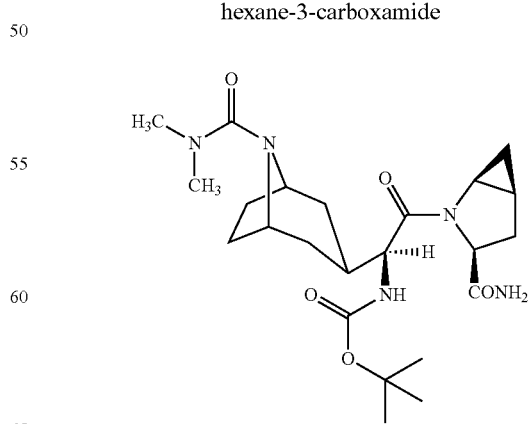

To a stirred solution of (2S)-2-(tert-butoxycarbonyl)-amino-2-[8-(dimethyl carbamoyl)-8-aza-bicyclo[3.2.1]-oct- 3-yl]-exo-ethanoic acid (1.0 g, 2.82 mmol) in DMF (10 ml) was added 1-hydroxybenzotriazole monohydrate (1.3 g, 8.46 mmol) and TFA salt of (1S,3S,5S)2-azabicyclo[3.1.0]-hexane-3-carboxamide (which can be prepared by using method as provided in WO 2004/052850, 0.676 g, 2.82 mmol) at room temperature. This reaction mixture was cooled to 0° C. and added triethyl amine (0.85 g, 1.2 ml, 8.46 mmol) and 1-(3-dimethyl amino propyl)-3-ethyl carbodiimide hydrochloride (1.08 g, 5.64 mmol). The reaction mixture was then brought to room temperature in 15 minutes and stirred at room temperature for 18 hours. The solvent was removed under reduced pressure, diluted with ethyl acetate (60 ml), washed with a saturated sodium bicarbonate solution (20 ml), water (15 ml) and brine (10 ml). The organic layer was dried over anhydrous $Na_2SO_4$ and the solvent was evaporated to get a crude product, which was purified by column chromatography over silica gel (100-200 mesh) using methanol:$NH_3$ in chloroform:dichloromethane in the ratio of 3:10:87 as an eluent to yield the title compound (0.5 g, 59%).

mp: 110-112° C.

MS: m/z 464 (M+1)

$^1$H NMR (CDCl$_3$+D$_2$O, 400 MHz): δ 0.80-0.87 (m, 1H), 0.95-1.02 (m, 1H), 1.42 (s, 9H), 1.48-1.65 (m, 6H), 1.70-1.78 (m, 1H), 1.85-1.92 (m, 2H), 2.24-2.40 (m, 2H), 2.45 (dd, J=2.4, 13.2 Hz, 1H), 2.85 (s, 6H), 3.6-3.66 (m, 1H), 4.04-4.14 (m, 2H), 4.54 (dd, J=6.8, 8.8 Hz, 1H), 4.82 (dd, J=2.4, 10.8 Hz, 1H), 5.27 (d, J=9.6 Hz, 1H),

Step 4: (1S,3S,5S)-2-{(2S)-2-(test-Butoxycarbonyl)-amino-2-[8-(dimethyl carbamoyl)-8-aza-bicyclo[3.2.1]-oct-3-yl]-exo-ethanoyl}-2-azabicyclo[3.1.0]-hexane-3-carbonitrile

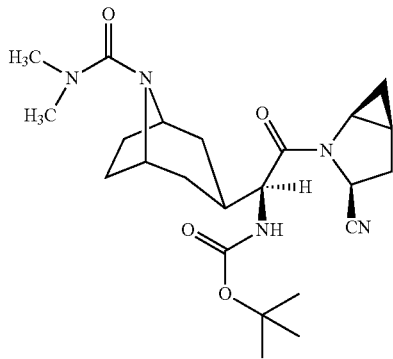 [SMILES: CN(C)C(=O)N1C2CCC1CC([C@H](NC(=O)OC(C)(C)C)C(=O)N1[C@H](C#N)C[C@@H]3C[C@@H]31)C2]

To a stirred solution of (1S,3S,5S)-2-{(2S)-2-(tert-butoxycarbonyl)-amino-2-[8-(dimethyl carbamoyl)-8-aza-bicyclo[3.2.1]-oct-3-yl]-exo-ethanoyl}-2-azabicyclo[3.1.0]-hexane-3-carboxamide (0.485 g, 1.05 mmol) and imidazole (0.15 g, 2.2 mmol) in dry pyridine (10 ml) was added phosphorousoxychloride (0.658 g, 0.39 ml, 4.3 mmol) drop wise at −30° C. under $N_2$ atmosphere. The reaction mixture was stirred at −30° C. for 90 minutes and quenched with water (1 ml) at −30° C. It was allowed to come to room temperature and the solvent was removed under reduced pressure at the same temperature. The crude product so obtained was dried under high vacuum and added dichloromethane (50 ml), washed with water (10 ml), dried over anhyd. $Na_2SO_4$. The solvent was evaporated to obtain a crude product, which was purified by column chromatography over silica gel (100-200 mesh) using 2% methanol in dichloromethane as an eluent to yield the title compound (0.35 g, 75%).

mp: 121-122° C.

MS: m/z 446 (M+1)

$^1$H NMR (CDCl$_3$, 400 MHz): δ 1.0-1.11 (m, 2H), 1.42 (s, 9H), 1.50-1.70 (m, 6H), 1.84-1.97 (m, 3H), 2.26-2.42 (m, 2H), 2.54-2.63 (m, 1H), 2.87 (s, 6H), 3.77-3.85 (m, 1H), 4.05-4.16 (m, 2H), 4.48 (t, J=8.4 Hz, 1H), 5.0 (dd, J=2.0, 10.4 Hz, 1H), 5.17 (d, J=9.2 Hz, 1H)

Step 5: (1S,3S,5S)-2-{(2S)-2-Amino-2-[8-(dimethyl carbamoyl)-8-aza-bicyclo[3.2.1]-oct-3-yl]-exo-ethanoyl}-2-azabicyclo[3.1.0]-hexane-3-carbonitrile trifluoro acetic acid salt

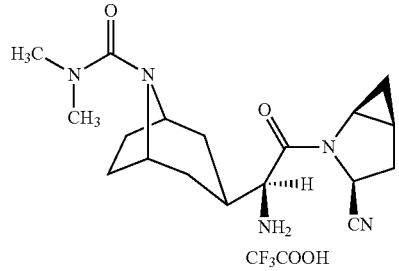 [SMILES: CN(C)C(=O)N1C2CCC1CC([C@H](N)C(=O)N1[C@H](C#N)C[C@@H]3C[C@@H]31)C2 ; "CF3COOH"]

To a stirred cooled (0° C.) solution of (1S,3S,5S)-2-{(2S)-2-(tert-butoxycarbonyl)amino-2-[8-(dimethyl carbamoyl)-8-aza-bicyclo[3.2.1]-oct-3-yl]-exo-ethanoyl}-2-azabicyclo[3.1.0]-hexane-3-carbonitrile (0.335 g, 0.75 mmol) in dichloromethane (3.5 ml) was added a solution of trifluoro acetic acid (3.5 ml, 5.36 g, 47 mmol) in dichloromethane (3.5 ml) drop wise at 0° C. The reaction mixture was stirred at 0° C. for 5 minutes, brought to room temperature and stirred at room temperature for 45 min. The solvent was evaporated under reduced pressure at 30° C. and added dichloromethane (20 ml). The solvent was again evaporated and dried under high vacuum. In order to solidify the product, petroleum ether (20 ml) was added and evaporated. This process was repeated twice. To remove traces of trifluoroacetic acid, the reaction mixture was stirred at room temperature with diethyl ether (2×15 ml) and filtered to yield the title compound (0.295 g, 85%).

mp: 178-180° C.

MS: m/z 346 (M+1)

$^1$H NMR (D$_2$O, 400 MHz): δ 0.91-0.97 (m, 1H), 1.14-1.22 (m, 1H), 1.53-1.80 (m, 6H), 1.83-1.95 (m, 2H), 2.0-2.07 (m, 1H), 2.41 (dd, J=2.0, 13.6 Hz, 1H), 2.63-2.77 (m, 2H), 2.86 (s, 6H), 3.73-3.79 (m, 1H), 4.14-4.22 (m, 2H), 4.48 (d, J=6 Hz, 1H), 5.16 (dd, J=2.0, 10.8 Hz, 1H),

EXAMPLE 2

(2S,5R)-1-{(2S)-2-Amino-2-[8-(dimethyl carbamoyl)-8-aza-bicyclo[3.2.1]oct-3-yl]-exo-ethanoyl}-5-ethynyl-pyrrolidin-2-carbonitrile trifluoro acetic acid salt (Compound 2)

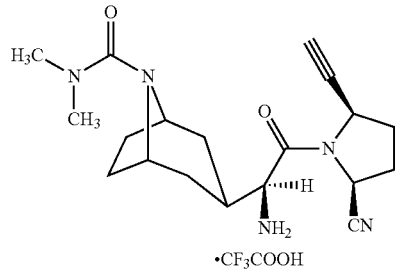 [SMILES: C#C[C@H]1CC[C@@H](C#N)N1C(=O)[C@@H](N)C1CC2CCC(C1)N2C(=O)N(C)C ; "·CF3COOH"]

Step 1: (2S,5R)-1-{(2S)-2-(tert-butoxy carbonyl)-amino-2-[8-(dimethyl carbamoyl)-8-aza-bicyclo[3.2.1]-oct-3-yl]-exo-ethanoyl}-5-ethynyl-pyrrolidin-2-carboxamide

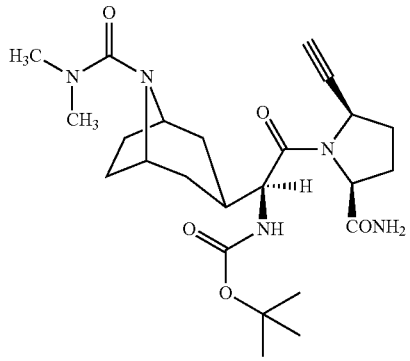 [SMILES: C#C[C@H]1CC[C@@H](C(N)=O)N1C(=O)[C@@H](NC(=O)OC(C)(C)C)C1CC2CCC(C1)N2C(=O)N(C)C]

To a stirred solution of (2S)-2-(tert-butoxycarbonyl)-amino-2-[8-(dimethyl carbamoyl)-8-aza-bicyclo[3.2.1]-oct-3-yl]-exo-ethanoic acid (Step-1 of Example 1, 1.2 g, 3.38 mmol) in dry DMF (15 ml) was added 1-hydroxybenzotriazole monohydrate (1.55 g, 10.14 mmol) and 5-ethynyl-pyrrolidin-2-carboxamide trifluoro acetic acid salt (which can be prepared by the procedure provided in WO 2008/011499 and WO 2009/037719 A1, 0.85 g, 3.38 mmol) at room temperature. The reaction mixture was cooled to 0° C. and added 1-(3-dimethyl amino propyl)-3-ethyl carbodimide hydrochloride (1.3 g, 6.76 mmol) followed by triethyl amine (1.41 ml, 1.02 g, 10.14 mmol). The reaction mixture was stirred at 0° C. for 5 minutes and then at room temperature for 18 hours. The solvent was evaporated under reduced pressure at 35° C. To this residue, was added water (15 ml) and extracted with ethyl acetate (3×50 ml). The combined organic layer was washed with a saturated sodium bicarbonate solution (15 ml) and dried over anhydrous $Na_2SO_4$. The solvent was evaporated under reduced pressure to get a crude product, which was purified by column chromatography over silica gel (100-200 mesh) using 2% methanol in dichloromethane as an eluent to yield the title compound (0.46 g, 29%).

MS: m/z 476 (M+1)

$^1$H NMR (CDCl$_3$, 400 MHz): δ 1.32-1.66 (m, 14H), 1.70-1.80 (m, 1H), 1.82-1.94 (m, 2H), 2.10-2.25 (m, 3H), 2.28-2.52 (m, 2H), (d, J=2.0 Hz, 1H), 2.85 (s, 6H), 4.03-4.12 (m, 2H), 4.42 (dd, J=7.6, 9.2 Hz, 1H), 4.54 (t, J=7.6, Hz, 1H), 5.05-5.14 (m, 2H), 5.47-5.54 (m, 1H), 6.35-6.45 (m, 1H).

Step 2: (2S,5R)-1-{(2S)-2-(tert-Butoxycarbonyl)-amino-2-[8-(dimethyl carbamoyl)-8-aza-bicyclo[3.2.1]-oct-3-yl]-exo-ethanoyl}-5-ethynyl-pyrrolidin-2-carbonitrile

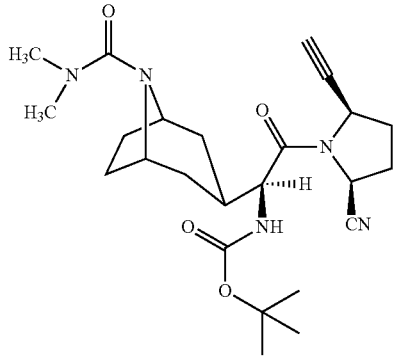 [SMILES: C#C[C@H]1CC[C@@H](C#N)N1C(=O)[C@@H](NC(=O)OC(C)(C)C)C1CC2CCC(C1)N2C(=O)N(C)C]

To a stirred solution of (2S,5R)-1-{(2S)-2-(tert-Butoxycarbonyl)-amino-2-[8-(dimethyl carbamoyl)-8-aza-bicyclo[3.2.1]-oct-3-yl]-exo-ethanoyl}-5-ethynyl-pyrrolidin-2-carboxamide (0.41 g, 0.863 mmol) and imidazole (0.117 g, 1.72 mmol) in dry pyridine (7.0 ml) was added phosphorousoxychloride (0.32 ml, 0.53 g, 3.45 mmol) dropwise at −35° C. under nitrogen atmosphere. The reaction mixture was then stirred at −20° C. to −10° C. for 3.0 hours. The completion of reaction was monitored by TLC. After completion, the reaction mixture was quenched with water (2 ml) at −30° C. and then it was allowed to come to room temperature. The solvent was removed under reduced pressure. The crude product was taken in water (20 ml) and extracted with dichloromethane (3×50 ml). The combined organic layers were dried over anhydrous $Na_2SO_4$, filtered and concentrated at reduced pressure to yield a crude product; which was purified by column chromatography over silica gel (100-200 mesh) using 2% methanol in dichloromethane as an eluant to obtain the title compound (0.31 g, 79%). mp: 88-90° C.

MS: m/z 458 (M+1)

$^1$H NMR (CDCl$_3$+D$_2$O, 400 MHz): δ 1.40 (s, 9H), 1.49-1.70 (m, 5H), 1.71-1.80 (m, 1H), 1.82-1.94 (m, 2H), 2.15-2.56 (m, 6H), 2.86 (s, 6H), 4.03-4.14 (m, 2H), 4.29 (t, J=8.0 Hz, 1H), 4.67 (t, J=8.4 Hz, 1H), 5.04 (d, J=8.8 Hz, 1H), 5.15-5.21 (m, 1H).

Step 3: (2S,5R)-1-{(2S)-2-Amino-2-[8-(dimethyl carbamoyl)-8-aza-bicyclo[3.2.1]oct-3-yl]-exo-ethanoyl}-5-ethynyl-pyrrolidin-2-carbonitrile trifluoro acetic acid salt

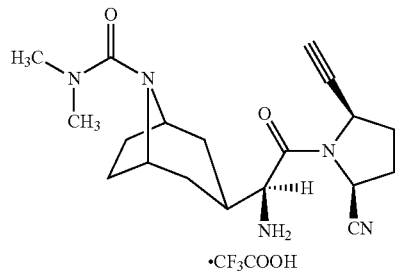 [SMILES: C#C[C@H]1CC[C@@H](C#N)N1C(=O)[C@@H](N)C1CC2CCC(C1)N2C(=O)N(C)C ; "·CF3COOH"]

To a stirred solution of (2S,5R)-1-{(2S)-2-(tert-butoxycarbonyl)-amino-2-[8-(dimethyl carbamoyl)-8-aza-bicyclo[3.2.1]-oct-3-yl]-exo-ethanoyl}-5-ethynyl-pyrrolidin-2-carbonitrile (0.30 g, 0.656 mmol) in dry dichloromethane (3 ml) was added a solution trifluoroacetic acid (3.0 ml, 4.44 g, 38.94 mmol) in dry dichloromethane (3 ml) at 0° C. After the addition was completed, reaction mixture was stirred at room temperature for 30 minutes. The solvent was evaporated under reduced pressure at 30° C. and added dichloromethane (20 ml). The solvent was again evaporated and dried under high vacuum. In order to solidify the product, petroleum ether (10 ml) was added and evaporated. The solid product was then washed with diethyl ether (2×10 ml) and dried under high vacuum for four hours to yield the title compound (0.265 g, 86%).

mp: 165-167° C.

MS: m/z 358 (M+1)

$^1$H NMR (D$_2$O, 400 MHz): δ 1.48-1.56 (m, 1H), 1.6-1.74 (m, 4H), 1.77-1.93 (m, 3H), 2.13-2.23 (m, 1H), 2.25-2.33 (m, 1H), 2.52-2.62 (m, 2H), 2.75-2.88 (m, 7H), 3.13 (d, J=2.4 Hz, 1H), 4.13-4.22 (m, 2H), 4.38 (d, J=6.0 Hz, 1H), 4.77-4.85 (m, 1H), 5.01 (d, J=7.2 Hz, 1H),

Demonstration of In Vitro Efficacy of Test Compounds

Inhibition of Human Recombinant DPP-IV

The proteolytic activity of human recombinant DPP-IV was determined by following the hydrolysis of Gly-Pro-7- amino-4-methylcoumarin (Gly-Pro-AMC) and the fluorometric quantitation of the liberated AMC. Assays were routinely carried out in 96-well flat-bottom black microwell plates. The reaction mixture (100 µl) contained 10 ng of human recombinant DPP-IV enzyme (produced in-house or procured from R&D Systems, USA) in the assay buffer (25 mM Tris-HCl, pH 7.4, 140 mM NaCl, 10 mM KCl and 0.1 mg/ml BSA) and 50 µM Gly-Pro-AMC. After incubation of assay plates at 30° C. for 30 min, the hydrolysis of Gly-Pro-AMC was monitored in a fluorescence microplate reader (Molecular Devices SpectraMax M5), with excitation and emission wavelengths set at 360 nm and 460 nm, respectively.

The inhibition of DPP-IV activity by test compounds was routinely performed by preincubating the enzyme with test compound (10 and 100 nM for primary screening and 8 concentrations from 0.1 to 1000 nM for the dose-response study) or vehicle (0.01% DMSO) for 15 min at 30° C., in a total volume of 90 µl. Test compounds were dissolved in DMSO at a concentration of 10 mM and serially diluted further in assay buffer. The enzyme reaction was initiated by the addition of Gly-Pro-AMC, followed by incubation of assay plates for 30 min at 30° C. and the liberated AMC was measured as described above. A known inhibitor of DPP-IV (positive control) was always included in the assay. Test compounds at various concentrations were always evaluated in duplicate, along with substrate blanks, vehicle controls and positive controls.

The results are expressed as percent inhibition of the enzyme activity relative to vehicle controls. Dose-response studies were conducted for those compounds exerting ≥50% inhibition of activity at 10 nM in primary screening. $IC_{50}$, defined as the inhibitor concentration which caused a 50% decrease of the activity under assay conditions, was computed using GraphPad Prism software, version 5.0.

The DPP-IV inhibition data (expressed either as $IC_{50}$ in nanomolar or percent inhibition at a particular compound concentration) is presented in Table 1.

TABLE 2

Inhibition of human recombinant DPP-IV

| Compound No. | $IC_{50}$, nM |
|---|---|
| 1 | 69% inhibition at 10 nM |
|   | 94.8% inhibition at 100 nM |
| 2 | 3.3 |

Demonstration of In Vivo Efficacy of Test Compounds

A. Measurement of Plasma DPP-IV Activity in Beagle Dogs

Overnight-fasted male animals were administered either vehicle or single oral dose of compound. Blood samples were collected prior to dosing and for 12 hours post dose into tubes containing EDTA. EDTA-plasma was separated and DPP-IV activity was measured using a fluorometric assay. Assays were carried out in 96-well flat-bottom black microwell plates. A typical reaction contained 25 µl plasma, 50 µl of 50 µM substrate (Gly-Pro-AMC) and 25 µl assay buffer (25 mM Tris-HCl, pH 7.4, 140 mM NaCl, 10 mM KCl and 1% BSA) in a total reaction volume of 100 µl. Plasma samples were incubated with the substrate for 30 min at 30° C., following which the fluorescence was measured in a microplate fluorescence reader (POLARstar Galaxy), with excitation and emission wavelengths set at 360 nm and 460 nm, respectively.

Percent inhibition in plasma DPP-IV activity due to compounds was calculated by comparing with plasma from vehicle-treated animals.

Table II shows the ability of compound 2 to produce inhibition of plasma DPP-IV in male Beagle dogs

TABLE II

Inhibition of plasma DPP-IV activity in Beagle dogs

| Compound no. | Dose (mg/kg, p.o.) | Plasma DPP-IV Inhibition (%) | | | | | | | |
|---|---|---|---|---|---|---|---|---|---|
| | | 0.5 h | 1 h | 2 h | 3 h | 4 h | 6 h | 8 h | 10 h | 12 h |
| 2 | 3 | 91 | 85 | 92 | 90 | 85 | 72 | 68 | 67 | 62 |

The invention claimed is:

1. Compound of general formula A in exo configuration,

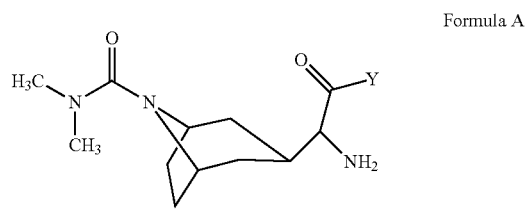

Formula A or an optical isomer, stereoisomer, racemate, or a pharmaceutically acceptable salt thereof, wherein,

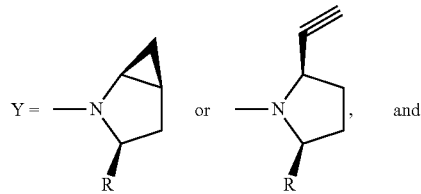

R = CN, CONH$_2$, or COOH.

2. A compound of general formula A, or an optical isomer, stereoisomer, racemate, or a pharmaceutically acceptable salt thereof, as claimed in claim 1 wherein the compound of the general formula (A) is selected from
    (2S,5R)-1-{(2S)-2-Amino-2-[8-(dimethyl carbamoyl)-8-aza-bicyclo[3.2.1]oct-3-yl]exo-ethanoyl}-5-ethynyl-pyrrolidin-2-carbonitrile; and
    (1S,3S,5S)-2-{(2S)-2-Amino[8-(dimethyl carbamoyl)-8-aza-bicyclo[3.2.1]-oct-3-yl]-exo-ethanoyl}-2-azabicyclo[3.1.0]-hexane-3-carbonitrile.

3. A pharmaceutical composition, which comprises a compound of formula (A) as defined in claim 1 and a pharmaceutically acceptable carrier, diluent, or excipients

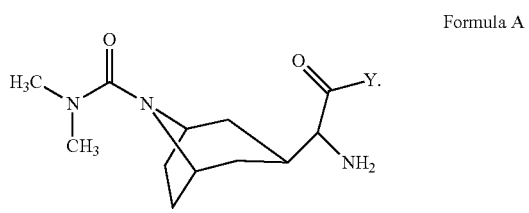

Formula A

4. A method of treating type-2 diabetes, which comprises administering a compound of formula (A) or a pharmaceutical composition as claimed in claim 3.

5. A process for preparation of a compound of formula (A),

Formula A

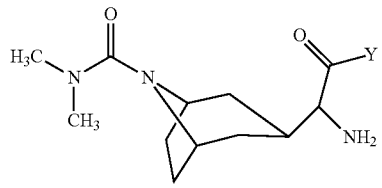

or an optical isomer, stereoisomer, racemate, or a pharmaceutically acceptable salt thereof, wherein,

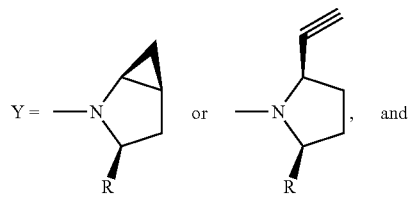

R = CN, CONH$_2$, or COOH;

which comprises the steps of:
(a) conversion of compound of formula I to compound of formula by a carbonyl insertion reaction between the compound of formula I and N,N dimethyl amine using triphosgene or di-tert-butyl dicarbonate or 1,1-carbonyl his imidazole and diisopropyl ethyl amine; or
conversion of compound of formula to compound of formula II by treating compound of formula I with dimethyl carbamoyl chloride in dichloromethane in presence of a base selected from triethyl amine and diisopropyl ethyl amine at temperature selected from 0° C. to 40° C. for a suitable time

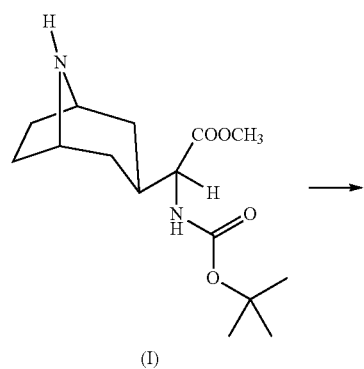

(I)

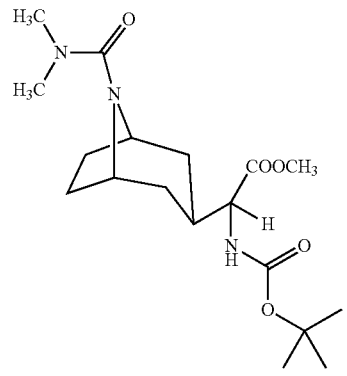

(II)

(b) hydrolysis of the ester group of compound of formula II in presence of a base selected from K$_2$CO$_3$, Na$_2$CO$_3$, and LiOH in a solvent selected from methanol, water and mixtures thereof at a temperature selected from 0° C.-30° C. for 15-20 hours to obtain the compound of formula III;

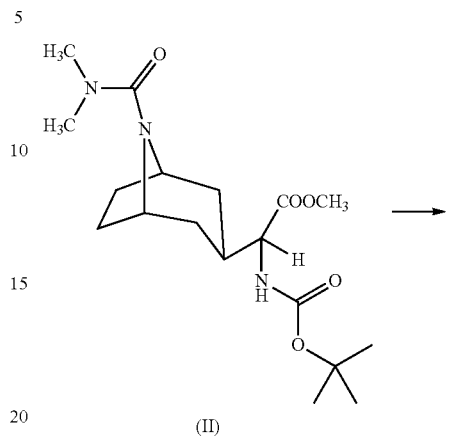

(II)

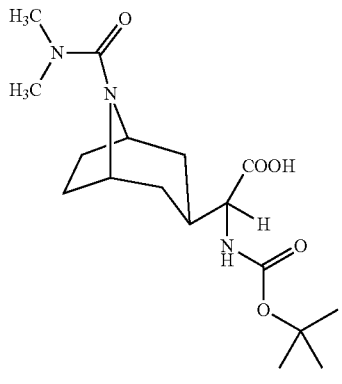

(III)

(c) conversion of compound of formula III to compound of formula V by condensation with compound of formula IV under standard peptide coupling conditions using EDCI, dicyclohexyl carbodiimide, HOBT optionally in presence of base selected from triethyl amine and diisopropylethyl amine in N,N-dimethylformamide at a temperature ranging between about 0 and 35° C.; isolation of the product formed using standard techniques; and purification using suitable organic solvent;

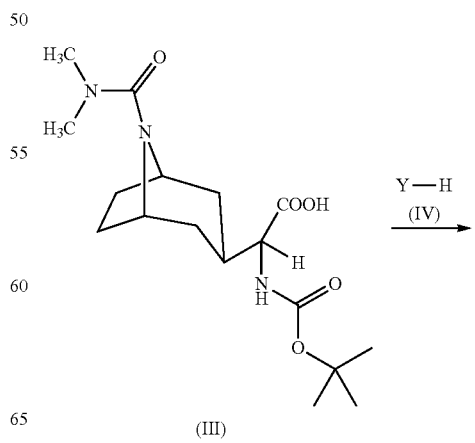

(III)

-continued

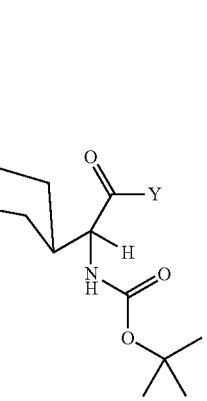

(V)

wherein,

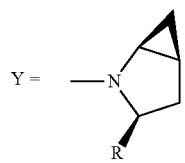 or 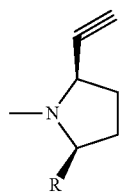 and

R = CONH₂ or COOH;

wherein,
- if R is CONH₂, then the CONH₂ group is optionally converted to CN by treatment with POCl₃; or
- if R is COOH, then the COOH group is optionally converted to CN by converting it to CONH₂ and then treating said CONH₂ with POCl₃;
- (d) deprotection using trifluoroacetic acid in dichloromethane at a temperature between 0 and 30° C.

6. The process as claimed in claim 5, wherein the compound of formula V

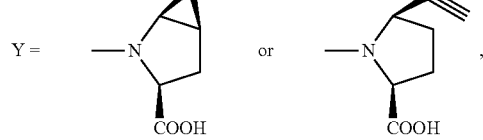

(V)

wherein,

Y = 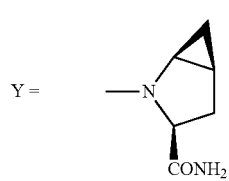 or 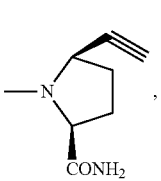, is converted to compound of formula (V) wherein

Y = 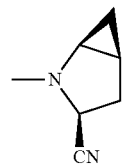 or 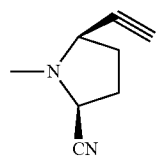

by treatment of POCl₃.

7. The process as claimed in claim 5, wherein the compound of formula V

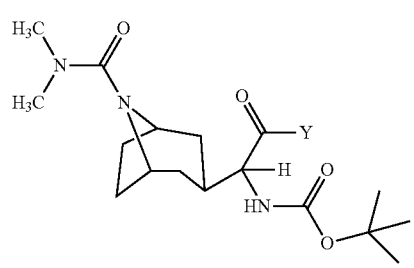

(V)

wherein,

Y = 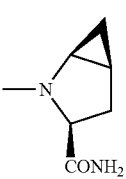 or 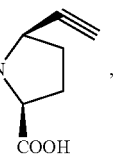

is converted to compound of formula (V) wherein

Y = 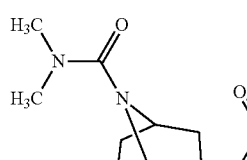

and is further converted to compound of formula (V) wherein

Y = 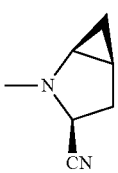 or 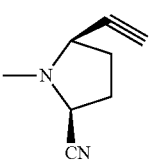

by treatment of POCl₃.

* * * * *